(12) United States Patent
Sommadossi et al.

(10) Patent No.: US 6,545,007 B2
(45) Date of Patent: Apr. 8, 2003

(54) METHODS FOR INHIBITING THE TRANSMISSION OF HIV USING TOPICALLY APPLIED SUBSTITUTED 6-BENZYL-4-OXOPYRIMIDINES

(75) Inventors: Jean-Pierre Sommadossi, Cambridge, MA (US); Martin L. Bryant, Carlisle, MA (US); Marino Artico, Rome (IT); Paolo La Colla, Cagliari (IT)

(73) Assignees: Idenix (Cayman) Limited, Grand Cayman (KY); Universita Degli Studi di Cagliari, Monserrato (IT)

( * ) Notice: Subject to any disclaimer, the term of this patent is extended or adjusted under 35 U.S.C. 154(b) by 0 days.

(21) Appl. No.: 10/001,868

(22) Filed: Nov. 19, 2001

(65) Prior Publication Data

US 2003/0008887 A1 Jan. 9, 2003

Related U.S. Application Data

(60) Provisional application No. 60/249,532, filed on Nov. 17, 2000.

(51) Int. Cl.⁷ .................. A61K 31/513; C07D 239/50
(52) U.S. Cl. .................. 514/274; 544/312; 544/314
(58) Field of Search .................. 514/274; 544/312, 544/314

(56) References Cited

U.S. PATENT DOCUMENTS

| 3,956,302 A | 5/1976 | Hunter et al. |
| 6,117,904 A | 9/2000 | Murphy et al. |
| 6,177,437 B1 * | 1/2001 | Wright .................. 514/274 |
| 6,376,504 B1 * | 4/2002 | Uckun et al. .................. 514/274 |

FOREIGN PATENT DOCUMENTS

| WO | WO 91/18887 | 12/1991 |
| WO | WO 95/18109 | 7/1995 |
| WO | WO 97/43266 | 11/1997 |
| WO | WO 00/03998 | 1/2000 |
| WO | WO 92/16201 | 9/2000 |

OTHER PUBLICATIONS

Nizi et al., Solid Phase Synthesis of 2,6–Disubstituted–4(3H)–pyrimidinones Targeting HIV–1 Reverse Transcriptase; Tetrahedron Letters 39; (1998); pp. 3307–3310.

Liu et al. Chem Abst. 121:108682.
Ife et al. Chem Abst. 116:128961.
Carter et al. Chem Abst. 116:194341.
Brown et al., Chem Abst. 109:210995.
Aroyan et al., Chem Abst. 75:49022.
Wagle et al., Chem Abst. 71:111298.
U.S. patent application Ser. No. 09/744,038, Artico et al., filed May 1, 2001.
Botta, M. et al. Eur. J. Med. Chem. 1992, 27, 251–257.
Artico M. et al. Antiviral Chem. Chemother. 1993, 4, 361–368.
Tramontano E. et al. Microbiologica 1994, 17, 269–279.
Massa S. et al. Antiviral Chem. Chemother. 1995, 6, 1–8.
Mai A. et al. J. Med. Chem. 1995, 38, 3258–3263.
Mai A. et al. J. Med. Chem. 1997, 40, 1447–1454.
Mai A. et al. J. Med. Chem. 1999, 42, 619–627.
Sbardella G. et al. Antiviral Chem. Chemother. 2001, 12, 37–50.
Sbardella G. et al. Med. Chem. Res. 2000, 10, 30–39.
Costi R. et al. Antiviral Chem. Chemother. 2000, 11, 117–133.
Balzarini J. et al. Molecular Pharmacology 1993, 44, 694–701.
Masanori Baba et al. Antimicrobial Agents & Chemother. 1994, 38, 688–692.
Fenner H. et al. Arch. Pharm. 1978, 311:2, 115–125 (Abstract only; Chem Abst. vol. 88, No. 21 Abst. 152555q).
Hiromichi Tanaka et al. J. Med. Chem. 1995, 38, 2860.

* cited by examiner

*Primary Examiner*—James H. Reamer
(74) *Attorney, Agent, or Firm*—Sherry M. Knowles, Esq.; Clark G. Sullivan, Esq.; King & Spalding LLP

(57) ABSTRACT

A method for inhibiting sexual transmission of HIV comprising topically applying to the skin or epithelial tissue of a human a composition comprising a non-nucleoside reverse transcriptase inhibitor ("NNRTI") that is able to inhibit viral replication for periods exceeding 12, 24, or even 36 days, at concentrations below even 10 $\mu$M. In one embodiment the NNRTI is a dihydro-alkyloxy-benzyl-oxopyrimidine (DABO).

43 Claims, 3 Drawing Sheets

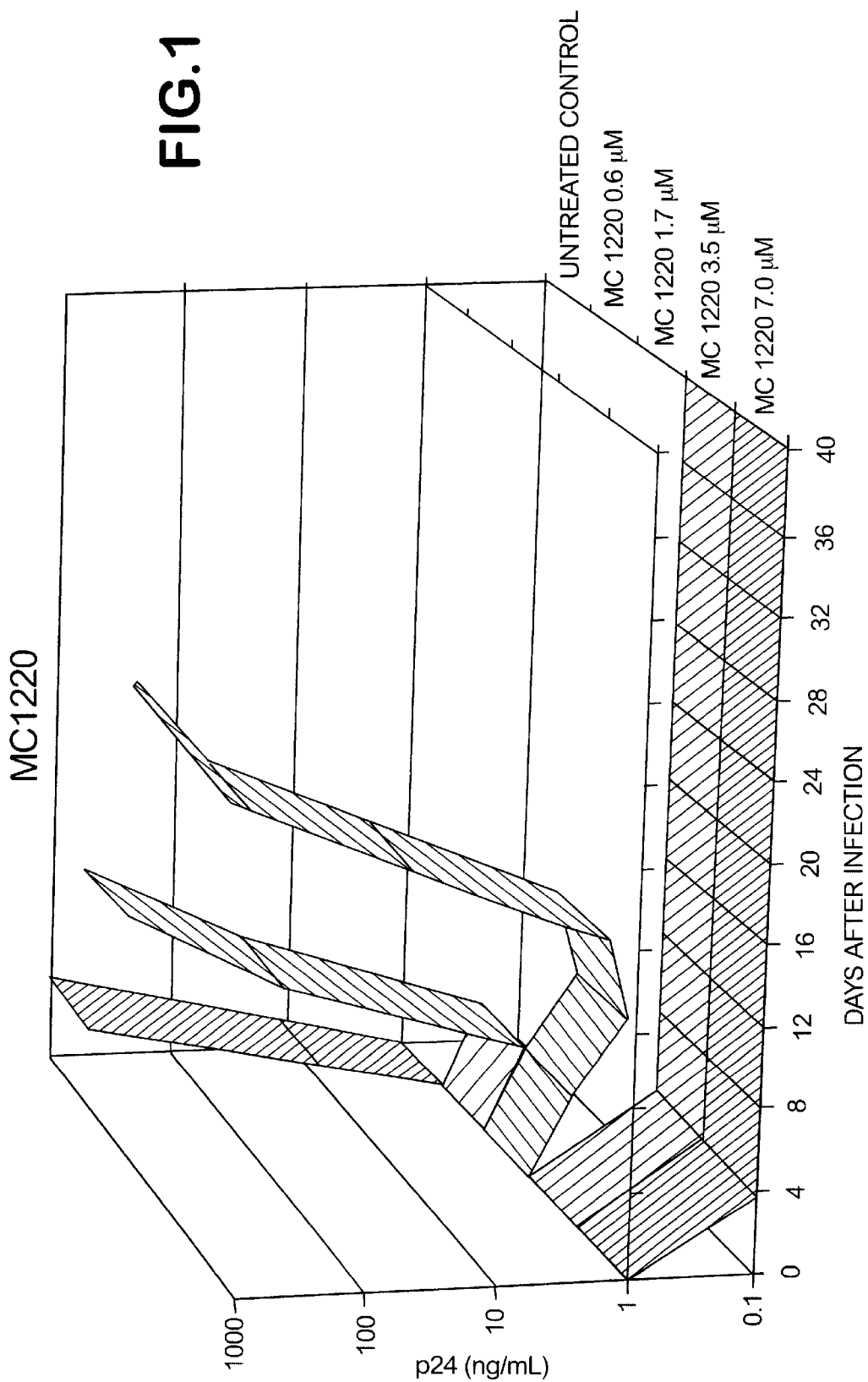

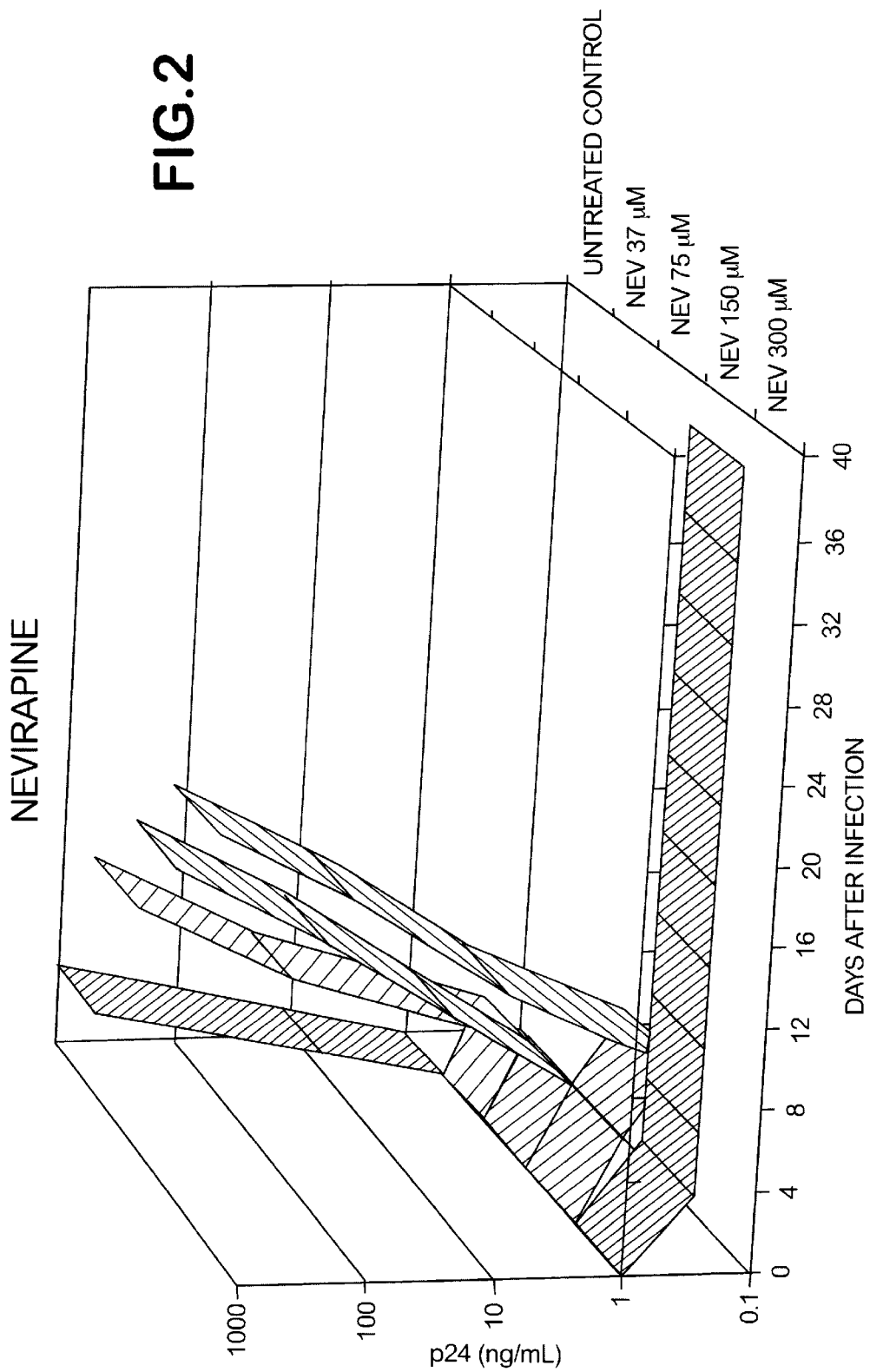

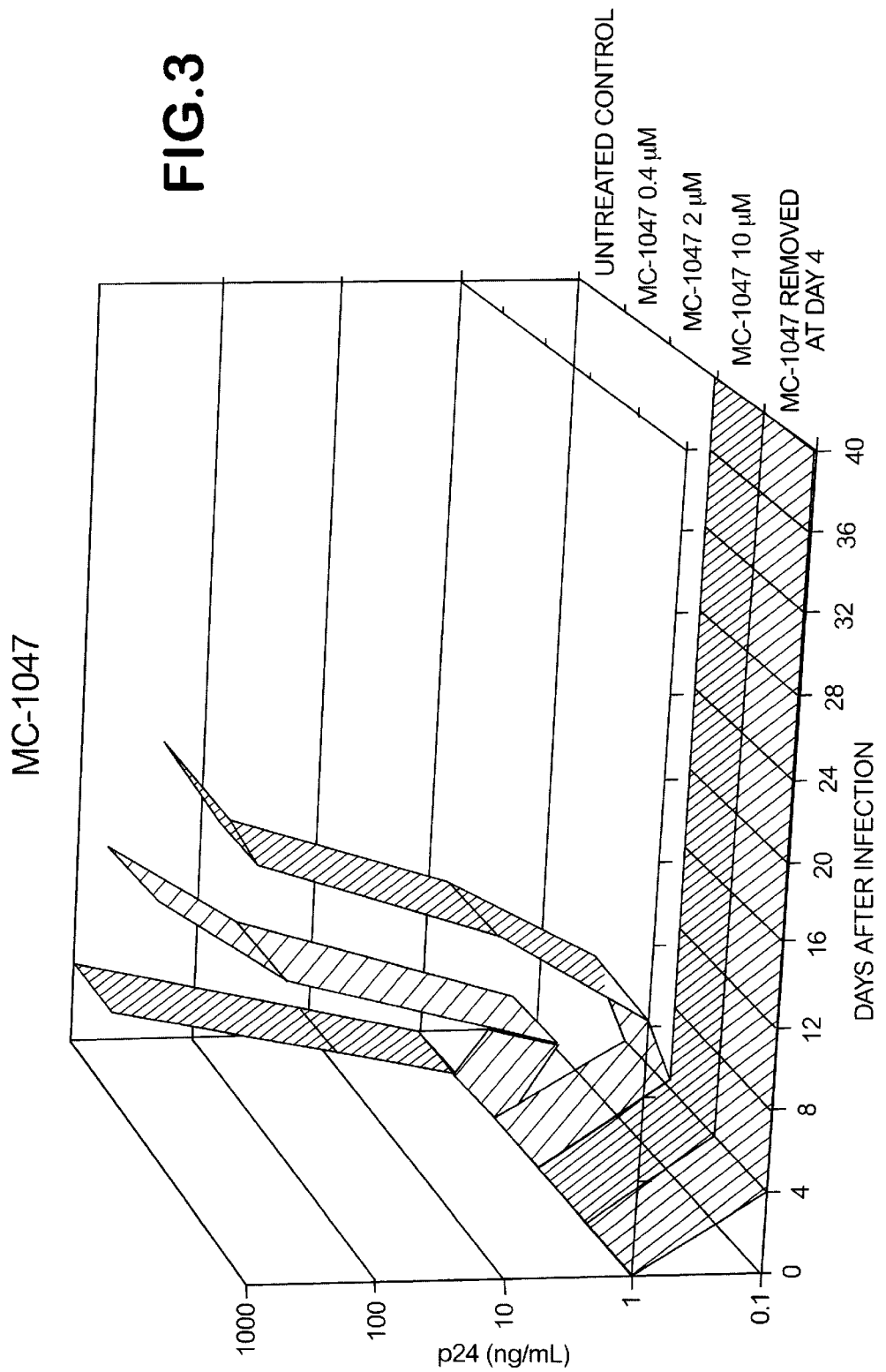

METHODS FOR INHIBITING THE TRANSMISSION OF HIV USING TOPICALLY APPLIED SUBSTITUTED 6-BENZYL-4-OXOPYRIMIDINES

CROSS REFERENCE TO RELATED APPLICATIONS

This application claims priority to provisional application serial No. 60/249,532, filed Nov. 17, 2000.

FIELD OF THE INVENTION

The present invention is compounds, methods, compositions, and devices for preventing infection by sexually transmitted HIV.

BACKGROUND OF THE INVENTION

The retrovirus designated human immunodeficiency virus (HIV) is the etiological agent of the complex disease that includes progressive destruction of the immune system (acquired immune deficiency syndrome; AIDS) and degeneration of the central and peripheral nervous system. Since it emerged as a public health threat in the early 1980's, efforts to control or eradicate the disease have focused principally on options for treating the disease after an individual has already become infected.

The use of condoms provides a substantial degree of protection against transmission of HIV infections during sexual intercourse. However, the use of condoms is not 100% effective against the transmission of HIV. Moreover, couples often do not use condoms. A topical composition that could be inserted into the vagina or rectum by a foam, gel, sponge or other form, or which could be topically applied to the male genitalia, would in many cases be preferred over condoms. Moreover, the prophylactic effectiveness of condoms could be improved by including a suitable microbicide in the lubricant coated on the exterior of the condom. However, to date little progress has been made to develop an effective topical composition against the transmission of HIV.

Most work to develop topical HIV prophylactic compositions has focused on the use of surfactants and buffers, such as the over-the-counter product nonoxynol-9. Surfactants and detergents disrupt microbial and sperm membranes by lysis and emulsification. Surfactant-containing creams and gels have the advantage of being very broad in their killing ability, and thus can kill the HIV virus and viruses associated with other sexually transmitted diseases. The use of surfactants and buffers is, however, substantially limited by the damage they can cause to cell membranes. In the vagina, nonoxynol-9 has been shown to thin vaginal walls. In the rectum, nonoxynol-9 can cause rectum walls to slough off.

Other virusidal compositions being investigated for use as HIV virusides include carageenan and other large sulfated polysaccharides that stick to viral envelopes and possibly shield cell membranes. Philips D M, "Of Mice and Men—Assaying Vaginal Virusides," Virusides 2000, Mar. 13–16, 2000, Alexandria Va., page 12, abstract A20. Monoclonal antibodies have also been proposed as HIV prophylactics, and some antibodies have shown a promising degree of protection. (Mascola J et al., "Role of IgG Antibody in Protection against Vaginal Transmission of an HIV-1/SIV Chimeric Virus," Virusides 2000, Mar. 13–16, 2000, Alexandria Va., page 7, abstract A10; Watanabe, M., Boyson, J. E., Lord, C. I. and Letvin, N. L. "Chimpanzees Immunized with Recombinant Soluble CD4 Develop Anti-self CD4 Antibody Responses with Anti-human Immunodeficiency Virus Activity", Proc. Natl. Acad. Sci. U.S.A., 89, 5103–5107 (1992); and Perno, C. -F., Baseler, M. W., Broder, S. and Yarchoan, R., "Infection of Monocytes by Human Immunodeficiency Virus Type 1 Blocked by Inhibitors of CD4-gp120 Binding, Even in the Presence of Enhancing Antibodies", J. Exp. Med., 171, 1043–1056 (1990)).

International application published as WO 00/03998 to P. LaColla and M. Artico disclosed substituted 6-benzyl-4-oxopyrimidines useful in the treatment of HIV.

Elise A. Sudbeck, Chen Mao, Rakesh Vig, T. K. Venkatachalam, Lisa Tuel-Ahlgren, and Fatih M. Uckun disclose various dihydroalkoxybenzyloxopyrimidine derivatives shown to be effective against HIV, which were designed based on structure analysis of potent nonnucleoside inhibitors of the human immunodeficiency virus reverse transcriptase.

Scientists have recently reported several biological discoveries that improve our understanding of how HIV enters an organism following sexual contact, which could lead to prophylactic substances that interfere with HIV's interaction with its target cells. These discoveries revolve generally around T lymphocytes, monocytes/macrophages and dendritic cells, suggesting that CD4 cell receptors are engaged in the process of virus transmission (Parr, M. B. and Parr, E. L., "Langerhans Cells and T lymphocyte Subsets in the Murine Vagina and Cervix", Biology of Reproduction, 44, 491–498 (1991); Pope, M. et al., "Conjugates of Dendritic Cells and Memory T Lymphocytes from Skin Facilitate Productive Infection With HIV-1", Cell, 78, 389–398 (1994); and Wira, C. R. and Rossoll, R. M., "Antigen-presenting Cells in the Female Reproductive Tract: Influence of Sex Hormones on Antigen Presentation in the Vagina", Immunology, 84, 505–508 (1995)). Geijtenbeek TBH et al., for example, recently reported that HIV tightly binds the DC—SIGN molecule on the surface of dendritic cells, through the gp120 HIV envelope protein. When the dendritic cells present microbial antigens to CD4+ T helper cells to stimulate an immune response, the dendritic cell inadvertently transfers the HIV to the CD4+ T cells, thereby advancing the progression of the infection.

Some have postulated, based upon these discoveries, that prophylactics can be designed that block the interaction between DC—SIGN and gp120. Similarly, DC4 and chemokine receptor blockers could be designed and administered to prevent the transfer of HIV from the dendritic cells to the CD4+ T cells. However, methods that rely on the specific interaction of HIV and human cells are limited, because the infection pathway has not been fully defined and may be diverse. (Miller, C. J. et al., "Genital Mucosal Transmission of Simian Immunodeficiency Virus: Animal Model for Heterosexual Transmission of Human Immunodeficiency Virus", J. Virol., 63, 4277–4284 (1989); Phillips, D. M. and Bourinbaiar, A. S., "Mechanism of HIV Spread from Lymphocytes to Epithelia", Virology, 186, 261–273 (1992); Phillips, D. M., Tan, X., Pearce-Pratt, R. and Zacharopoulos, V. R., "An Assay for HIV Infection of Cultured Human Cervix-derived Cells", J. Virol. Methods, 52, 1–13 (1995); Ho, J. L. et al., "Neutrophils from Human Immunodeficiency Virus (HIV)-SeronegatiVe Donors Induce HIV Replication from HIV-infected Patients Mononuclear Cells and Cell lines": An In Vitro Model of HIV Transmission Facilitated by Chlamydia Trachomatis., "J. Exp. Med., 181, 1493–1505 (1995); and Braathen, L. R. & Mork, C. in "HIV infection of Skin Langerhans Cells", In:

Skin Langerhans (dendritic) cells in virus infections and AIDS (ed. Becker, Y.) 131–139 (Kluwer Academic Publishers, Boston, (1991)).

Efforts by researchers to develop an HIV vaccine have also not yet been successful. Siegel et al. reported that vaccination with inactivated SIV did not protect African Green monkeys against infection with the homologous virus notwithstanding a strong immune response to SIV. (Siegel, F., Kurth, R., and Norley, S., (1995), "Neither Whole Inactivated Virus Immunogen nor Passive Immunoglobulin Transfer Protects Against SIV Infection in the African Green Monkey Natural Host", J. AIDS, 8, 217–226).

Therefore, there remains a need for an effective topical prophylactic against the sexual transmission of HIV. It is an object of the invention, therefore, to provide topical prophylactic compositions against the sexual transmission of HIV, methods for using such compositions, and devices that deliver such compositions.

It is another object of the invention to provide compounds that have extended activity against the HIV virus.

It is another object of this invention to provide a topical composition that can be applied to the areas of skin and mucus epithelia at highest risk for exchanging HIV pathogens. Formulations of such compositions can be based upon existing topical compositions used as lubricants and contraceptives, which are often present as lotions or gels, or coated to the exterior of condoms.

It is another object of this invention to create new, long-term prophylactic methods for women based upon existing contraceptive devices, including sustained release devices to be inserted in the vagina (intra-vaginal devices such as sponges and cervical caps).

It is still another object of this invention to provide suppositories and intra-vaginal or rectal pills that can be inserted into the vagina or rectum in order to release one or more anti-HIV agents at a predetermined rate.

Yet another object of the invention is to deliver, along with the anti-HIV agent, agents against other things from which the user desires protection, such as sperm, toxins, and/or STD pathogens.

SUMMARY OF THE INVENTION

The invention provides compounds, compositions and methods for prophylactically inhibiting the spread of AIDS. The compounds of the present invention display inhibition of HIV replication, and do so for a prolonged period of time, which renders them useful in prophylactic applications, wherein the frequency or duration of use are not always predictable. The compounds are also useful in prophylactic applications because they inhibit the HIV virus upon contact at very low concentrations, before the virus has infected its host and begun replication. Non-nucleoside reverse transcriptase inhibitors ("NNRTI") have proven especially invaluable in this type of application.

Thus, in one embodiment, the invention provides a method for inhibiting sexual transmission of HIV comprising topically applying to the skin or epithelial tissue of a human a composition comprising a non-nucleoside reverse transcriptase inhibitor ("NNRTI") that is able to inhibit viral replication for periods exceeding 12, 24 or even 36 days, at concentrations below even 10 $\mu$M.

In one embodiment the NNRTI is a dihydro-alkyloxy-benzyl-oxopyrimidine (DABO). This class of compounds is capable of inhibiting HIV multiplication targeting reverse transcriptase without bioactivation. Preferred DABOs include compounds of formula (A):

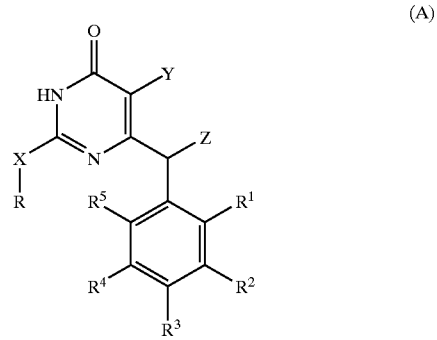

as herein defined.

In another embodiment the invention provides a topical composition in the form of a cream, lotion, gel, or foam, comprising a dihydro-alkyloxy-benzyl-oxopyrimidine.

In still another embodiment the invention provides a composition in the form of an intra-vaginal or intra-rectal pill or suppository comprising a dihydro-alkyloxy-benzyl-oxopyrimidine.

A still further embodiment provides a device for inhibiting the sexual transmission of HIV comprising: (a) a barrier structure for insertion into the vaginal cavity, and (b) a composition comprising a dihydro-alkyloxy-benzyl-oxopyrimidine.

Still a further embodiment provides dihydro-alkyloxy-benzyl-oxopyrimidines defined by the foregoing structure.

BRIEF DESCRIPTION OF THE DRAWINGS

FIG. 1 is a three dimensional line graph showing the levels of viral p24 in cell culture supernatants treated with the specified concentrations of MC 1220.

FIG. 2 is a three dimensional line graph showing the levels of viral p24 in cell culture supernatants treated with the specified concentrations of Nevirapine.

FIG. 3 is a three dimensional line graph showing the levels of viral p24 in cell culture supernatants treated with the specified concentrations of MC-1047.

DETAILED DISCUSSION OF THE INVENTION

In one aspect the invention provides a composition and method for inhibiting sexual transmission of HIV comprising topically applying to the skin or epithelial tissue of a human a composition comprising a non-nucleoside reverse transcriptase inhibitor ("NNRTI") that is able to inhibit viral replication for periods exceeding 12, 24, or even 36 days. In separate embodiments, the composition is able to inhibit viral replication for such prolonged periods at concentrations as low as 50, 35, 20, 10 or 5 $\mu$M. The ability of a compound to inhibit viral replication is preferably evaluated by the HIV-1 p24 antigen enzyme-linked immunosorbent assay. Suitable ELISA kits are available, for example, from Abbott Laboratories. Particular methods for their use are set forth in the examples herein. The ability of a non-nucleotide compound to inhibit reverse transcriptase can also be assessed by the methods set forth in the examples hereof.

The composition is preferably applied topically to any skin or epithelial tissue that comes in contact with bodily fluids of a sexual partner during sexual intercourse or foreplay, including the vaginal endothelium, the rectal endothelium or the male genitalia. As used herein, the term "topical application" refers to something that is applied to and spread across the surface of the skin or a mucous membrane (by contrast, "systemic" administration refers to a drug or other compound that is ingested orally or injected beneath the skin). A condom lubricant or other genital lubricant is a topical agent as that term is used herein.

In one particular embodiment the NNRTI is a dihydro-alkyloxy-benzyl-oxo-pyrimidine, as defined further herein.

Preferred compositions can take several forms. Thus, in one embodiment the composition is in the form of a cream, lotion, gel, or foam that is applied to the affected skin or epithelial cavity, and preferably spread over the entire skin or epithelial surface which is at risk of contact with bodily fluids. Such formulations, which are suitable for vaginal or rectal administration, may be present as aqueous or oily suspensions, solutions or emulsions (liquid formulations) containing in addition to the active ingredient, such carriers as are known in the art to be appropriate. For "stand-alone" lubricants (i.e., lubricants that are not pre-packaged with condoms), gels and similar aqueous formulations are generally preferred, for various reasons (both scientific and economic) known to those skilled in the art. These formulations are useful to protect not only against sexual transmission of HIV, but also to prevent infection of a baby during passage through the birth canal. Thus the vaginal administration can take place prior to sexual intercourse, during sexual intercourse, and immediately prior to childbirth.

One method of applying an anti-viral lubricant to the genitals, for the purposes disclosed herein, involves removing a small quantity (such as a teaspoon, or several milliliters) of a gel, cream, ointment, emulsion, or similar formulation from a plastic or metallic tube, jar, or similar container, or from a sealed plastic, metallic or other packet containing a single dose of such composition, and spreading the composition across the surface of the penis immediately before intercourse. Alternate methods of emplacement include: (1) spreading the composition upon accessible surfaces inside the vagina or rectum shortly before intercourse; and (2) emplacing a condom, diaphragm, or similar device, which has already been coated or otherwise contacted with an anti-viral lubricant, upon the penis or inside the vagina. In a preferred embodiment, any of these methods of spreading an anti-viral lubricant across the surfaces of the genitals causes the lubricant to coat and remain in contact with the genital and epithelial surfaces throughout intercourse.

In one embodiment the compositions are used in conjunction with condoms, to enhance the risk-reducing effectiveness of condoms and provide maximum protection for users. The composition can either be coated onto condoms during manufacture, and enclosed within conventional watertight plastic or foil packages that contain one condom per package, or it can be manually applied by a user to either the inside or the outside of a condom, immediately before use.

As used herein, "condom" refers to a barrier device which is used to provide a watertight physical barrier between male and female genitalia during sexual intercourse, and which is removed after intercourse. This term includes conventional condoms that cover the penis; it also includes so-called "female condoms" which are inserted into the vaginal cavity prior to intercourse. The term "condom" does not include diaphragms, cervical caps or other barrier devices that cover only a portion of the epithelial membranes inside the vaginal cavity. Preferably, condoms should be made of latex or a synthetic plastic material such as polyurethane, since these provide a high degree of protection against viruses.

In another embodiment the composition is in the form of an intra-vaginal pill, an intra-rectal pill, or a suppository. The suppository or pill should be inserted into the vaginal or rectal cavity in a manner that permits the suppository or pill, as it dissolves or erodes, to coat the vaginal or rectal walls with a prophylactic layer of the anti-HIV agent.

In still another embodiment the composition is topically applied by release from an intravaginal device. Devices such as vaginal rings, vaginal sponges, diaphrams, cervical caps, female condoms, and the like can be readily adapted to release the composition into the vaginal cavity after insertion.

Compositions used in the methods of this invention may also comprise other active agents, such as another agent to prevent HIV infection, and agents that protect individuals from conception and other sexually transmitted diseases. Thus, in another embodiment the compositions used in this invention further comprise a second anti-HIV agent, a virucide effective against viral infections other than HIV, and/or a spermicide.

In one particular embodiment, the composition contains nonoxynol, a widely-used spermicidal surfactant. The resulting composition could be regarded as a "bi-functional" composition, since it would have two active agents that provide two different desired functions, in a relatively inert carrier liquid; the nonoxynol would provide a spermicidal contraceptive agent, and the DABO would provide anti-viral properties. The nonoxynol is likely to cause some level of irritation, in at least some users; this is a regrettable but is a well-known side effect of spermicidal surfactants such as nonoxynol and octoxynol, which attack and destroy the lipid bilayer membranes that surround sperm cells and other mammalian cells.

The compositions used in this invention may also contain a lubricant that facilitates application of the composition to the desired areas of skin and epithelial tissue, and reduces friction during sexual intercourse. In the case of a pill or suppository, the lubricant can be applied to the exterior of the dosage form to facilitate insertion.

In still another embodiment the invention provides a device for inhibiting the sexual transmission of HIV comprising (a) a barrier structure for insertion into the vaginal cavity, and (b) a composition comprising a dihydro-alkyloxy-benzyl-oxopyrimidine. As mentioned above, preferred devices which act as barrier structures, and which can be adapted to apply anti-HIV agent, include the vaginal sponge, diaphram, cervical cap, or condom (male or female).

The methods, compositions and devices of this invention can be adapted generally to release active agent in a time sensitive manner that best corresponds to the timing of sexual activity. When topically applied as a lotion or gel, the compositions are preferably applied immediately prior to sexual activity. Other modes of application, such as devices and suppositories, can be designed to release active agent over a prolonged period of time, at a predetermined rate, depending upon the needs of the consumer.

Dihydro-alkyloxy-benzyl-oxopyrimidines

The dihydro-alkyloxy-benzyl-oxopyrimidines of this invention are preferably defined by formula A described below, combinations thereof, or pharmaceutically acceptable salts thereof:

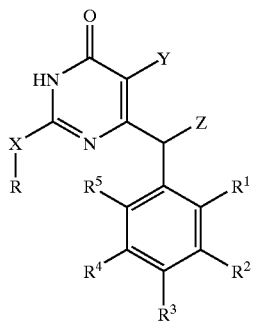

(A)

A principle embodiment is defined wherein:

X is —O, —CH$_2$, —CHK$^1$ (wherein K$^1$ is —H, —C$_{1-4}$ alkyl, —C$_{3-6}$Cycloalkyl), —S, —NK$^2$ (wherein K$^2$ is —H, —C$_{1-4}$alkyl, —C$_{3-6}$cycloalkyl, or a bond when X—R is nitro), -aryl, or -arylalkyl;

R is —H, —C$_{1-4}$alkyl (optionally containing one or more of heteroatoms selected from O, S, and N), —C$_{3-6}$ cycloalkyl (optionally containing one or more of heteroatoms selected from O, S, N), -aryl, -arylakl, heterocycle, oxo, thio, or a primary amine;

Y is —H, —C$_{1-4}$alkyl or —C$_{3-6}$cycloalkyl;

Z is —H, —C$_{1-4}$alkyl or —C$_{3-6}$cycloalkyl;

R$^1$ is —H, —C$_{1-4}$alkyl, -halogen, —NO$_2$, ΔOW (wherein W is —H, —CH$_3$, aryl), or —SW (wherein W is —H, —CH$_3$, -aryl);

R$^2$ is —H, —C$_{1-4}$alkyl, -halogen, —NO$_2$, —OW (wherein W is —H, —CH$_3$, -aryl); or —SW (wherein W is —H, —CH$_3$, -aryl);

R$^3$ is —H, —C$_{1-4}$alkyl, -halogen, —NO$_2$, —OW (wherein W is —H, —CH$_3$, -aryl); or —SW (wherein W is —H, —CH$_3$, -aryl);

R$^4$ is —H, —C$_{1-4}$alkyl, -halogen, —NO$_2$, —OW (wherein W is —H, —CH$_3$, -aryl); or —SW (wherein W is —H, —CH$_3$,-aryl); and R$^5$ is —H, —C$_{1-4}$alkyl, -halogen, —NO$_2$, —OW (wherein W is —H, —CH$_3$, -aryl), or —SW (wherein W is —H, —CH$_3$, -aryl).

A first principal class of 13 subembodiments are defined when:

1. Y is —C$_{1-4}$alkyl, Z is —C$_{1-4}$alkyl, and X, R, R$^1$, R$^2$, R$^3$, R$^4$ and R$^5$ are as defined above in the principal embodiment;
2. Y is methyl, Z is methyl, and X, R, R$^1$, R$^2$, R$^3$, R$^4$ and R$^5$ are as defined above in the principal embodiment;
3. R$^1$ and R$^5$ are halogen, and Y, Z, X, R, R$^2$, R$^3$ and R$^4$ are as defined above in the principal embodiment;
4. R$^1$ and R$^5$ are fluorine, and Y, Z, X, R, R$^2$, R$^3$ and R$^4$ are as defined above in the principal embodiment;
5. R$^2$, R$^3$ and R$^4$ are hydrogen, and Y, Z, X, R, R$^1$ and R$^5$ are as defined above in the principal embodiment;
6. Y is —C$_{1-4}$alkyl, Z is —C$_{1-4}$alkyl, R$^1$ and R$^5$ are halogen, and X, R, R$^2$, R$^3$ and R$^4$ are as defined above in the principal embodiment;
7. Y is methyl, Z is methyl, R$^1$ and R$^5$ are fluorine, and X, R, R$^2$, R$^3$ and R$^4$ are as defined above in the principal embodiment;
8. Y is —C$_{1-4}$alkyl, Z is —C$_{1-4}$alkyl, R$^2$, R$^3$ and R$^4$ are hydrogen, and X, R, R$^1$ and R$^5$ are as defined above in the principal embodiment;
9. Y is methyl, Z is methyl, R$^2$, R$^3$ and R$^4$ are hydrogen, and X, R, R$^1$ and R$^5$ are as defined above in the principal embodiment;
10. R$^1$ and R$^5$ are halogen, R$^2$, R$^3$ and R$^4$ are hydrogen, and X, R, Y and Z are as defined above in the principal embodiment;
11. R$^1$ and R$^5$ are fluorine, R$^2$, R$^3$ and R$^4$ are hydrogen, and X, R, Y and Z are as defined above in the principal embodiment;
12. Y is —C$_{1-4}$alkyl, Z is —C$_{1-4}$alkyl, R$^1$ and R$^5$ are halogen, R$^2$, R$^3$ and R$^4$ are hydrogen, and X and R are as defined above in the principal embodiment; and
13. Y is methyl, Z is methyl, R$^1$ and R$^5$ are fluorine, R$^2$, R$^3$ and R$^4$ are hydrogen, and X and R are as defined above in the principal embodiment.

A second principal class of subembodiments are defined when:

1. —X is NK, and Y, Z, R, R$^1$, R$^2$, R$^3$, R$^4$ and R$^5$ are as defined in any one of the first class of thirteen subembodiments;
2. —X is NK, R is H, and Y, Z, X, R$^1$, R$^2$, R$^3$, R$^4$ and R$^5$ are as defined in any one of the first class of thirteen subembodiments;
3. —X—R is —N-Me$_2$, and Y, Z, X, R$^1$, R$^2$, R$^3$, R$^4$ and R$^5$ are as defined in any one of the first class of thirteen subembodiments;
4. —X—R is —NH-cPe (cyclic pentane), and Y, Z, X, R$^1$, R$^2$, R$^3$, R$^4$ and R$^5$ are as defined in any one of the first class of thirteen subembodiments;
5. —X—R is —N=O, and Y, Z, X, R, R$^1$, R$^2$, R$^3$, R$^4$ and R$^5$ are as defined in any one of the first class of thirteen subembodiments;
6. —X is S, and Y, Z, X, R, R$^1$, R$^2$, R$^3$, R$^4$ and R$^5$ are as defined in any one of the first class of thirteen subembodiments;
7. —X—R is —S-Me, and Y, Z, X, R$^1$, R$^2$, R$^3$, R$^4$ and R$^5$ are as defined in any one of the first class of thirteen subembodiments;
8. —X—R is —S-MeSMe, and Y, Z, X, R$^1$, R$^2$, R$^3$, R$^4$ and R$^5$ are as defined in any one of the first class of thirteen subembodiments; and
9. —X—R is —S-cPe, and Y, Z, X, R$^1$, R$^2$, R$^3$, R$^4$ and R$^5$ are as defined in any one of the first class of thirteen subembodiments.

Preferred species of dihydro-alkyloxy-benzyl-oxopyrimidines are defined when:

1. —X—R is —N-Me$_2$, Y is methyl, Z is methyl, R$^1$ and R$^1$ are fluorine, and R$^2$, R$^3$ and R$^4$ are hydrogen (MC 1220);
2. —X—R is —NH-cPe (cyclic pentane), Y is methyl, Z is methyl, R$^1$ and R$^5$ are fluorine, and R$^2$, R$^3$ and R$^4$ are hydrogen (MC 1129);
3. —X—R is —N=O, Y is methyl, Z is methyl, R$^1$ and R$^1$ are fluorine, and R$^2$, R$^3$ and R$^4$ are hydrogen (MC 1237);
4. —X—R is —S-Me, Y is methyl, Z is methyl, R and R$^1$ are fluorine, and R$^2$, R$^3$, and R$^4$ are hydrogen (MC 1060);
5. —X—R is —S-MeSMe, Y is methyl, Z is methyl, R$^1$ and R$^5$ are fluorine, and R$^2$, R$^3$ and R$^4$ are hydrogen (MC 1214); and
6. —X—R is —S-cPe, Y is methyl, Z is methyl, R$_1$ and R$_5$ are fluorine, and R$_2$, R$_3$, and R$_4$ are hydrogen (MC 1047).

Other preferred species of dihydro-alkyloxy-benzyl-oxopyrimidines are those listed in table 1 and table 2.

TABLE 1

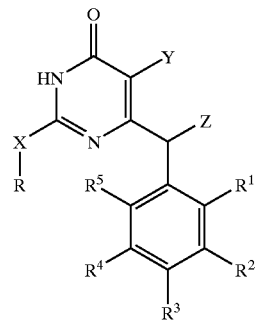

Physical and Chemical Data of MC Compounds

| Compd. | X | Y | Z | R | $R^1$ | $R^2$ | $R^3$ | $R^4$ | $R^5$ | m.p., °C | Recryst. Solvent | % yield | Formula [a] |
|---|---|---|---|---|---|---|---|---|---|---|---|---|---|
| MC 507 | O | H | H | 2,5-Me$_2$-c-hex | H | H | H | H | H | 130–132 | Petrol. Ether/diethyl ether | 22 | $C_{19}H_{24}N_2O_2$ |
| MC 508 | O | H | H | 4,5-Me$_2$-c-hex | H | H | H | H | H | 132–134 | Petrol. Ether/diethyl ether | 28 | $C_{19}H_{24}N_2O_2$ |
| MC 512 | O | H | H | 3,5-Me$_2$-c-hex | H | H | H | H | H | 178–181 | Petrol. Ether/diethyl ether | 12 | $C_{19}H_{24}N_2O_2$ |
| MC 531 | O | Me | H | 2,5-Me$_2$-c-hex | H | H | H | H | H | 196–198 | Petrol. Ether/diethyl ether | 18 | $C_{20}H_{26}N_2O_2$ |
| MC 1114 | O | H | H | Sec-but | F | H | H | H | F | 87–88 | Petrol. Ether/diethyl ether | 28 | $C_{15}H_{16}F_2N_2O_2$ |
| MC 1103 | O | H | H | c-pent | F | H | H | H | F | 183.5–184.5 | Benzene | 52 | $C_{16}H_{16}F_2N_2O_2$ |
| MC 843 | S | H | H | benzyl-oxymeth | H | H | H | H | H | 181–183 | Cyclohexane/benzene | 38 | $C_{19}H_{18}N_2O_2S$ |
| MC 796 | S | H | Ph | Sec-but | H | H | H | H | H | 157–158 | n-hexane/cyclohexane | 78 | $C_{21}H_{22}N_2OS$ |
| MC 890 | S | H | Me | Iso-prop | H | H | H | H | H | 118–119 | n-hexane | 88 | $C_{15}H_{18}N_2OS$ |
| MC 892 | S | H | Me | c-pent | H | H | H | H | H | 95–96 | n-hexane | 65 | $C_{17}H_{20}N_2OS$ |
| MC 898 | S | H | Me | c-hex | H | H | H | H | H | 142–143 | n-hexane | 59 | $C_{18}H_{22}N_2OS$ |
| MC 899 | S | H | Et | Iso-prop | H | H | H | H | H | 144–145 | Cyclohexane | 85 | $C_{16}H_{20}N_2OS$ |
| MC 900 | S | H | Et | c-pent | H | H | H | H | H | 168–169 | Cyclohexane | 69 | $C_{18}H_{22}N_2OS$ |
| MC 903 | S | H | Et | c-hex | H | H | H | H | H | 175.5–176.5 | Cyclohexane | 60 | $C_{19}H_{24}N_2OS$ |
| MC 806 | S | H | H | Sec-but | Me | H | H | H | H | 118–119 | n-hexane/cyclohexane | 67 | $C_{16}H_{20}N_2OS$ |
| MC 842 | S | H | H | c-pent | Me | H | H | H | H | 142–144 | Cyclohexane | 61 | $C_{17}H_{20}N_2OS$ |
| MC 809 | S | H | H | Sec-but | H | H | Me | H | H | 107.5–108.5 | n-hexane | 56 | $C_{16}H_{20}N_2OS$ |
| MC 817 | S | H | H | Sec-but | NO$_2$ | H | H | H | H | 148.0–148.5 | Cyclohexane/benzene | 68 | $C_{15}H_{17}N_3O_3S$ |
| MC 897 | S | H | H | Sec-but | H | NO$_2$ | H | H | H | 127–128 | Cyclohexane/benzene | 54 | $C_{15}H_{17}N_3O_3S$ |
| MC 863 | S | H | H | Sec-but | H | H | NO$_2$ | H | H | 128–130 | Petrol. Ether/diethyl ether | 100 | $C_{15}H_{17}N_3O_3S$ |
| MC 854 | S | H | H | Sec-but | Cl | H | H | H | H | 120–121 | n-hexane/cyclohexane | 58 | $C_{15}H_{17}N_3O_3S$ |
| MC 857 | S | H | H | Sec-but | H | Cl | H | H | H | 98–99 | Cyclohexane | 92 | $C_{15}H_{17}N_3O_3S$ |
| MC 859 | S | H | H | Sec-but | H | H | Cl | H | H | 125–126 | Cyclohexane | 74 | $C_{15}H_{17}ClN_2OS$ |
| MC 880 | S | H | H | Sec-but | F | H | H | H | H | 106–107 | n-hexane/cyclohexane | 68 | $C_{15}H_{17}ClN_2OS$ |
| MC 884 | S | H | H | Sec-but | H | F | H | H | H | 96–97 | Cyclohexane | 67 | $C_{15}H_{17}FN_2OS$ |
| MC 889 | S | H | H | Sec-but | H | H | F | H | H | 98–99 | n-hexane | 94 | $C_{15}H_{17}FN_2OS$ |
| MC 825 | S | H | H | Sec-but | NH$_2$ | H | H | H | H | 143–144 | Cyclohexane/benzene | 74 | $C_{15}H_{19}N_3OS$ |
| MC 960 | S | H | H | Sec-but | H | H | NH$_2$ | H | H | 128–130 | Cyclohexane | 77 | $C_{15}H_{19}N_3OS$ |
| MC 868 | S | H | H | Sec-but | CF$_3$ | H | H | H | H | 125–126 | Cyclohexane | 89 | $C_{16}H_{17}F_3N_2OS$ |
| MC 959 | S | H | H | Sec-but | H | H | CF$_3$ | H | H | 144–145 | Cyclohexane | 75 | $C_{16}H_{17}F_3N_2OS$ |
| MC 952 | S | H | H | Sec-but | OMe | H | H | H | H | 123–124 | Cyclohexane | 69 | $C_{16}H_{20}N_2O_2S$ |
| MC 957 | S | H | H | Sec-but | H | OMe | H | H | H | 78–80 | n-hexane/Cyclohexane | 71 | $C_{16}H_{20}N_2O_2S$ |
| MC 964 | S | H | H | Sec-but | H | H | OMe | H | H | 112–113 | Cyclohexane | 63 | $C_{16}H_{20}N_2O_2S$ |
| MC 1041 | S | H | H | Sec-but | H | F | H | H | H | 122–123 | Cyclohexane | 68 | $C_{15}H_{16}F_2N_2OS$ |
| MC 1042 | S | H | H | Sec-but | H | Me | H | H | H | 119–120 | n-hexane | 72 | $C_{17}H_{22}N_2OS$ |
| MC877 | S | H | H | Me | Cl | H | H | H | Cl | 237–238 | benzene | 98 | $C_{12}H_{10}Cl_2N_2OS$ |
| MC878 | S | H | H | iso-prop | Cl | H | H | H | Cl | 230–231 | benzene | 81 | $C_{14}H_{14}Cl_2N_2OS$ |
| MC886 | S | H | H | n-but | Cl | H | H | H | Cl | 153–154 | cyclohexane | 62 | $C_{15}H_{16}Cl_2N_2OS$ |
| MC885 | S | H | H | iso-but | Cl | H | H | H | Cl | 143.5–144.5 | cyclohexane | 56 | $C_{15}H_{16}Cl_2N_2OS$ |
| MC815 | S | H | H | sec-but | Cl | H | H | H | Cl | 183–184 | cyclohexane/benzene | 55 | $C_{15}H_{16}Cl_2N_2OS$ |
| MC888 | S | H | H | c-pent | Cl | H | H | H | Cl | 185–186 | cyclohexane | 54 | $C_{16}H_{16}Cl_2N_2OS$ |
| MC891 | S | H | H | c-hex | Cl | H | H | H | Cl | 200–201 | cyclohexane/benzene | 49 | $C_{17}H_{18}Cl_2N_2OS$ |
| MC871 | S | H | H | Me | F | H | H | H | F | 197–198 | benzene | 95 | $C_{12}H_{10}F_2N_2OS$ |
| MC860 | S | H | H | iso-prop | F | H | H | H | F | 174–175 | cyclohexane | 74 | $C_{14}H_{14}F_2N_2OS$ |
| MC872 | S | H | H | n-but | F | H | H | H | F | 126–127 | cyclohexane | 46 | $C_{15}H_{16}F_2N_2OS$ |
| MC866 | S | H | H | iso-but | F | H | H | H | F | 136–137 | cyclohexane | 49 | $C_{15}H_{16}F_2N_2OS$ |
| MC848 | S | H | H | sec-but | F | H | H | H | F | 149–150 | n-hexane/cyclohexane | 48 | $C_{15}H_{16}F_2N_2OS$ |
| MC867 | S | H | H | c-pent | F | H | H | H | F | 168–169 | cyclohexane | 45 | $C_{16}H_{16}FN_2OS$ |
| MC870 | S | H | H | c-hex | F | H | H | H | F | 164–165 | cyclohexane | 40 | $C_{17}H_{18}F_2N_2OS$ |

TABLE 1-continued

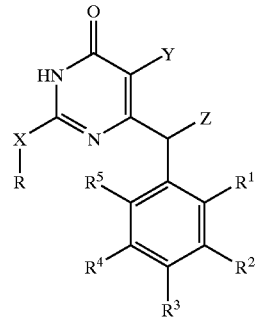

(A)

Physical and Chemical Data of MC Compounds

| Compd. | X | Y | Z | R | $R^1$ | $R^2$ | $R^3$ | $R^4$ | $R^5$ | m.p., °C. | Recryst. Solvent | % yield | Formula [a] |
|---|---|---|---|---|---|---|---|---|---|---|---|---|---|
| MC1001 | S | H | Me | iso-prop | Cl | H | H | H | Cl | 196–196.5 | cyclohexane/benzene | 52 | $C_{15}H_{16}Cl_2N_2OS$ |
| MC996 | S | H | Me | c-pent | Cl | H | H | H | Cl | 181–182 | cyclohexane | 45 | $C_{17}H_{18}Cl_2N_2OS$ |
| MC1016 | S | H | Me | c-hex | Cl | H | H | H | Cl | 211–212 | cyclohexane/benzene | 42 | $C_{18}H20Cl_2N_2OS$ |
| MC1000 | S | H | Et | iso-prop | Cl | H | H | H | Cl | 166–168 | diethyl ether | 54 | $C16H_{18}Cl_2N_2OS$ |
| MC1002 | S | H | Et | c-pent | Cl | H | H | H | Cl | 168–169 | diethyl ether | 40 | $C_{18}H_{20}Cl_2N_2OS$ |
| MC1003 | S | H | Et | c-hex | Cl | H | H | H | Cl | 198–199 | cyclohexane | 41 | $C_{19}H_{22}Cl_2N_2OS$ |
| MC1007 | S | H | Me | iso-prop | F | H | H | H | F | 155–156 | cyclohexane | 53 | $C_{15}H_{16}F_2N_2OS$ |
| MC1044 | S | H | Me | iso-but | F | H | H | H | F | 159–160 | cyclohexane | 49 | $C_{16}H_{18}F_2N_2OS$ |
| MC1045 | S | H | Me | n-but | F | H | H | H | F | 149–150 | cyclohexane | 58 | $C_{16}H_{18}F_2N_2OS$ |
| MC1110 | S | H | Me | sec-but | F | H | H | H | F | 133–134 | n-hexane | 75 | $C_{16}H_{18}F_2N_2OS$ |
| MC1008 | S | H | Me | c-pent | F | H | H | H | F | 165.5–166.5 | cyclohexane | 60 | $C_{17}H_{18}F_2N_2OS$ |
| MC1013 | S | H | Me | c-hex | F | H | H | H | F | 206–207 | benzene | 44 | $C_{18}H_{20}F_2N_2OS$ |
| MC1005 | S | H | Et | iso-prop | F | H | H | H | F | 149–150 | cyclohexane | 40 | $C_{16}H_{18}F_2N_2OS$ |
| MC1006 | S | H | Et | c-pent | F | H | H | H | F | 141–143 | cyclohexane | 45 | $C_{18}H_{20}F_2N_2OS$ |
| MC1014 | S | H | Et | c-hex | F | H | H | H | F | 154–155 | cyclohexane | 51 | $C_{19}H_{22}F_2N_2OS$ |
| MC971 | S | H | Me | iso-prop | CH=CH—CH=CH | H | H | H | 161–162 | n-hexane/cyclohexane | 58 | $C_{19}H_{20}N_2OS$ |
| MC972 | S | H | Me | c-pent | CH=CH—CH=CH | H | H | H | 140–141 | n-hexane/cyclohexane | 49 | $C_{21}H_{22}N_2OS$ |
| MC974 | S | H | Me | c-hex | CH=CH—CH=CH | H | H | H | 177–178 | n-hexane | 45 | $C_{22}H_{24}N_2OS$ |
| MC969 | S | H | Et | iso-prop | CH=CH—CH=CH | H | H | H | 163–164 | cyclohexane | 54 | $C_{20}H_{22}N_2OS$ |
| MC973 | S | H | Et | c-pent | CH=CH—CH=CH | H | H | H | oil | — | 48 | $C_{22}H_{24}N_2OS$ |
| MC975 | S | H | Et | c-hex | CH=CH—CH=CH | H | H | H | 126–127 | n-hexane | 41 | $C_{23}H_{26}N_2OS$ |
| MC844 | S | Me | H | sec-but | Me | H | H | H | H | 177–178 | cyclohexane | 55 | $C_{17}H_{22}N_2OS$ |
| MC845 | S | Me | H | sec-but | H | H | H | Me | H | 127–128 | n-hexane | 61 | $C_{17}H_{22}N_2OS$ |
| MC925 | S | Me | H | sec-but | H | $NO_2$ | H | H | H | 163–164 | cyclohexane/benzene | 88 | $C_{16}H_{19}N_3O_3S$ |
| MC924 | S | Me | H | sec-but | H | H | $NO_2$ | H | H | 178–180 | cyclohexane/benzene | 100 | $C_{16}H_{19}N_3O_3S$ |
| MC909 | S | Me | H | sec-but | Cl | H | H | H | H | 170–171 | cyclohexane | 68 | $C_{16}H_{19}ClN_2OS$ |
| MC910 | S | Me | H | sec-but | H | Cl | H | H | H | 145–146 | cyclohexane | 75 | $C_{16}H_{19}ClN_2OS$ |
| MC911 | S | Me | H | sec-but | H | H | Cl | H | H | 163–165 | cyclohexane | 79 | $C_{16}H_{19}ClN_2OS$ |
| MC913 | S | Me | H | sec-but | F | H | H | H | H | 120.5–121.5 | cyclohexane | 65 | $C_{16}H_{19}FN_2OS$ |
| MC918 | S | Me | H | sec-but | H | F | F | H | H | 146–147 | cyclohexane | 72 | $C_{16}H_{19}FN_2OS$ |
| MC919 | S | Me | H | sec-but | H | H | H | H | H | 154–155 | cyclohexane | 69 | $C_{16}H_{19}FN_2OS$ |
| MC912 | S | Me | H | Me | Cl | H | H | H | Cl | 206–261 | benzene | 93 | $C_{13}H_{12}Cl_2N_2OS$ |
| MC914 | S | Me | H | iso-prop | Cl | H | H | H | Cl | 241–242 | cyclohexane/benzene | 78 | $C_{15}H_{16}Cl_2N_2OS$ |
| MC920 | S | Me | H | n-but | Cl | H | H | H | Cl | 179–180 | cyclohexane | 52 | $C_{16}H_{18}Cl_2N_2OS$ |
| MC916 | S | Me | H | iso-but | Cl | H | H | H | Cl | 208–209 | cyclohexane | 63 | $C_{16}H_{18}Cl_2N_2OS$ |
| MC850 | S | Me | H | sec-but | Cl | H | H | H | Cl | 204–205 | cyclohexane | 53 | $C_{16}H_{18}Cl_2N_2OS$ |
| MC915 | S | Me | H | c-pent | Cl | H | H | H | Cl | 252–253 | cyclohexane/benzene | 49 | $C_{17}H_{18}Cl_2N_2OS$ |
| MC917 | S | Me | H | c-hex | Cl | H | H | H | Cl | 237–238 | cyclohexane | 48 | $C_{18}H_{20}Cl_2N_2OS$ |
| MC869 | S | Me | H | Me | F | H | H | H | F | 218.5–219.5 | benzene | 92 | $C_{13}H_{12}F_2N_2OS$ |
| MC881 | S | Me | H | iso-prop | F | H | H | H | F | 164–165 | cyclohexane | 76 | $C_{15}H_{16}F_2N_2OS$ |
| MC905 | S | Me | H | n-but | F | H | H | H | F | 178–179 | cyclohexane | 65 | $C_{16}H_{18}F_2N_2OS$ |
| MC921 | S | Me | H | iso-but | F | H | H | H | F | 161–162 | cyclohexane | 59 | $C_{16}H_{18}F_2N_2OS$ |
| MC849 | S | Me | H | sec-but | F | H | H | H | F | 128–129 | n-hexane | 49 | $C_{16}H_{18}F_2N_2OS$ |
| MC922 | S | Me | H | c-pent | F | H | H | H | F | 192–193 | cyclohexane | 54 | $C_{17}H_{18}F_2N_2OS$ |
| MC923 | S | Me | H | c-hex | F | H | H | H | F | 191–192 | cyclohexane | 49 | $C_{18}H_{20}F_2N_2OS$ |
| MC1060 | S | Me | Me | Me | F | H | H | H | F | 202–203 | cyclohexane/benzene | 49 | $C_{14}H_{14}F_2N_2OS$ |
| MC1109 | S | Me | Me | sec-but | F | H | H | H | F | 135–136 | cyclohexane | 55 | $C_{17}H_{20}F_2N_2OS$ |
| MC1047 | S | Me | Me | c-pent | F | H | H | H | F | 196–197 | cyclohexane | 60 | $C_{18}H_{20}F_2N_2OS$ |
| MC798 | S | Et | H | sec-but | H | H | H | H | H | 140–141 | n-hexane | 47 | $C_{17}H_{22}N_2OS$ |
| MC1037 | S | Et | H | iso-prop | F | H | H | H | F | 174–175 | benzene | 78 | $C_{16}H_{18}F_2N_2OS$ |
| MC1038 | S | Et | H | sec-but | F | H | H | H | F | 150–151 | n-hexane/cyclohexane | 62 | $C_{17}H_{20}F_2N_2OS$ |
| MC804 | S | Et | H | sec-but | CH=CH—CH=CH | H | H | H | 198.5–199.5 | cyclohexane | 42 | $C_{21}H_{24}N_2OS$ |
| MC1039 | S | i-pro | H | iso-prop | F | H | H | H | F | 167–168 | n-hexane | 76 | $C_{17}H_{20}F_2N_2OS$ |
| MC852 | S | allyl | H | sec-but | H | H | H | H | H | 127.5–128.5 | cyclohexane | 68 | $C_{18}H_{22}N_2OS$ |
| MC856 | S | n-pro | H | sec-but | H | H | H | H | H | 108–109 | n-hexane | 42 | $C_{18}H_{24}N_2OS$ |
| MC834 | S | n-but | H | sec-but | H | H | H | H | H | oil | — | 32 | $C_{19}H_{26}N_2OS$ |

TABLE 1-continued

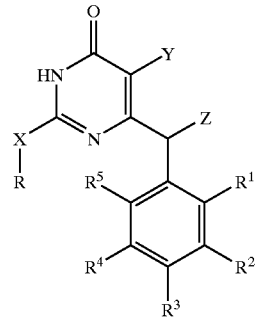

(A)

Physical and Chemical Data of MC Compounds

| Compd. | X | Y | Z | R | R¹ | R² | R³ | R⁴ | R⁵ | m.p., °C | Recryst. Solvent | % yield | Formula [a] |
|---|---|---|---|---|---|---|---|---|---|---|---|---|---|
| MC1119 | NH | H | H | ethyl | F | H | H | H | F | 138–140 | n-hexane/cyclohexane | 50 | $C_{13}H_{13}F_2N_3O$ |
| MC1078 | NH | H | H | n-prop | F | H | H | H | F | 136–137 | cyclohexane | 49 | $C_{14}H_{15}F_2N_3O$ |
| MC979 | NH | H | H | iso-prop | F | H | H | H | F | 150–151 | diethyl ether | 58 | $C_{14}H_{15}F_2N_3O$ |
| MC980 | NH | H | H | c-prop | F | H | H | H | F | 183–184 | cyclohexane/benzene | 68 | $C_{14}H_{13}F_2N_3O$ |
| MC1077 | NH | H | H | n-but | F | H | H | H | F | 130–131 | n-hexane | 60 | $C_{15}H_{17}F_2N_3O$ |
| MC945 | NH | H | H | sec-but | F | H | H | H | F | 140–141 | diethyl ether | 80 | $C_{15}H_{17}F_2N_3O$ |
| MC1043 | NH | H | H | MeOethyl | F | H | H | H | F | 120–121 | acetonitrile | 78 | $C_{14}H_{15}F_2N_3O_2$ |
| MC1022 | NH | H | H | c-pent | F | H | H | H | F | oil | — | 74 | $C_{16}H_{17}F_2N_3O$ |
| MC1049 | NH | H | H | c-hex | F | H | H | H | F | 143–144 | diethyl ether | 45 | $C_{17}H_{19}F_2N_3O$ |
| MC1048 | NH | H | Me | c-pent | F | H | H | H | F | oil | — | 48 | $C_{17}H_{19}F2N_3O$ |
| MC1118 | NH | Me | H | iso-prop | F | H | H | H | F | 165–166 | n-hexane | 53 | $C_{15}H_{17}F_2N_3O$ |
| MC1130 | NH | Me | H | sec-but | F | H | H | H | F | oil | — | 56 | $C_{16}H_{19}F_2N_3O$ |
| MC1050 | NH | Me | H | c-pent | F | H | H | H | F | 115–117 | n-hexane/cyclohexane | 60 | $C_{17}H_{19}F_2N_3O$ |
| MC1105 | NH | Me | H | benzyl | F | H | H | H | F | 182–183 | cyclohexane/benzene | 82 | $C_{19}H_{17}F_2N_3O$ |
| MC1129 | NH | Me | Me | c-pent | F | H | H | H | F | oil | — | 38 | $C_{18}H_{21}F_2N_3O$ |
| MC1167 | NH | H | H | Me | F | H | H | H | F | 202–203 | acetonitrile | 39 | $C_{12}H_{11}F_2N_3O$ |
| MC1168 | NH | Me | H | Me | F | H | H | H | F | 210–211 | acetonitrile | 48 | $C_{13}H_{13}F_2N_3O$ |
| MC1186 | NH | Me | H | n-prop | F | H | H | H | F | 156–157 | acetonitrile | 62 | $C_{15}H_{17}F_2N_3O$ |
| MC1185 | NH | Me | H | n-but | F | H | H | H | F | 192–193 | acetonitrile | 68 | $C_{16}H_{19}F_2N_3O$ |
| MC1178 | NH | H | Me | Me | F | H | H | H | F | 145–146 | acetonitrile | 34 | $C_{13}H_{13}F_2N_3O$ |
| MC1190 | NH | H | Me | n-prop | F | H | H | H | F | oil | — | 45 | $C_{15}H_{17}F_2N_3O$ |
| MC1191 | NH | H | Me | iso-prop | F | H | H | H | F | oil | — | 54 | $C_{15}H_{17}F_2N_3O$ |
| MC1189 | NH | H | Me | n-but | F | H | H | H | F | oil | — | 55 | $C_{16}H_{19}F_2N_3O$ |
| MC1192 | NH | H | Me | sec-but | F | H | H | H | F | oil | — | 59 | $C_{16}H_{19}F_2N_3O$ |
| MC1180 | NH | H | Me | c-hex | F | H | H | H | F | oil | — | 62 | $C_{18}H_{21}F_2N_3O$ |
| MC1170 | NH | Me | Me | Me | F | H | H | H | F | 193–194 | cyclohexane/benzene | 34 | $C_{14}H_{15}F_2N_3O$ |
| MC1187 | NH | Me | Me | n-but | F | H | H | H | F | oil | — | 49 | $C_{17}H_{21}F_2N_3O$ |
| MC1181 | NH | Me | Me | c-hex | F | H | H | H | F | oil | — | 54 | $C_{19}H_{23}F_2N_3O$ |
| MC1182 | N | H | H | Me₂ | F | H | H | H | F | 210–211 | cyclohexane/benzene | 88 | $C_{13}H_{13}F_2N_3O$ |
| MC1183 | N | H | H | Me-piperaz | F | H | H | H | F | 195–196 | acetonitrile | 84 | $C_{16}H_{18}F_2N_4O$ |
| MC1188 | N | H | H | morph | F | H | H | H | F | 215–216 | acetonitrile | 75 | $C_{15}H_{15}F_2N_3O_2$ |
| MC1193 | N | H | H | thiomorph | F | H | H | H | F | 233–234 | acetonitrile | 78 | $C_{15}H_{15}F_2N_3OS$ |
| MC1194 | N | H | H | piperid | F | H | H | H | F | 209–210 | acetonitrile | 68 | $C_{16}H_{17}F_2N_3O$ |
| MC1196 | N | H | H | pyrrolid | F | H | H | H | F | 233–234 | acetonitrile | 52 | $C_{15}H_{15}F_2N_3O$ |
| MC1202 | N | H | H | Et₂ | F | H | H | H | F | 159–160 | acetonitrile | 43 | $C_{15}H17F_2N_3O$ |
| MC1204 | N | H | H | (n-prop)₂ | F | H | H | H | F | 111–112 | n-hexane | 32 | $C_{17}H_{21}F_2N_3O$ |
| MC1195 | N | Me | H | Me₂ | F | H | H | H | F | 237–238 | acetonitrile | 80 | $C_{14}H_{15}F_2N_3O$ |
| MC1203 | N | Me | H | Me-piperaz | F | H | H | H | F | 235–236 | acetonitrile | 62 | $C_{17}H_{20}F_2N_4O$ |
| MC1205 | N | Me | H | morph | F | H | H | H | F | 244–245 | acetonitrile | 65 | $C_{16}H_{17}F_2N_3O_2$ |
| MC1206 | N | Me | H | thiomorph | F | H | H | H | F | 255–256 | acetonitrile | 54 | $C_{16}H_{17}F_2N_3OS$ |
| MC1137 | S | Me | Me | iso-prop | F | H | H | H | F | 177–178 | n-hexane/cyclohexane | 45 | $C_{16}H_{18}F_2N_2OS$ |
| MC1175 | S | Me | Me | n-but | F | H | H | H | F | 122–123 | n-hexane | 51 | $C_{17}H_{20}F_2N_2OS$ |
| MC1153 | S | Me | Me | iso-but | F | H | H | H | F | 152–153 | cyclohexane | 58 | $C_{17}H_{20}F_2N_2OS$ |
| MC1174 | S | Me | Me | c-hex | F | H | H | H | F | 208–209 | n-hexane/cyclohexane | 48 | $C_{19}H_{22}F_2N_2OS$ |
| MC1161 | S | H | H | MeSMe | F | H | H | H | F | 159–160 | cyclohexane/benzene | 72 | $C_{13}H_{12}F_2N_2OS_2$ |
| MC1162 | S | Me | H | MeSMe | F | H | H | H | F | 183–184 | cyclohexane/benzene | 70 | $C_{14}H_{14}F_2N_2OS_2$ |
| MC1157 | S | Et | H | MeSMe | F | H | H | H | F | 153–154 | cyclohexane | 69 | $C_{15}H_{16}F_2N_2OS_2$ |
| MC1145 | S | i-pro | H | MeSMe | F | H | H | H | F | 158.5–160 | cyclohexane | 62 | $C_{16}H_{18}F_2N_2OS_2$ |
| MC1140 | S | H | H | MeSMe | H | H | H | H | H | 117.5–118 | n-hexane | 64 | $C_{13}H_{14}N_2OS_2$ |

[a] All compounds were analyzed for C, H, N, S, and, when required, Cl and F; analytical results were within ±0.4% of therroretical values.

TABLE 2

Cytotoxicity and anti-HIV-1 Activity of MC Compounds.

| | | | | | | | | | | {μM} | | |
| Compd. | X | Y | Z | R | R¹ | R² | R³ | R⁴ | R⁵ | $CC_{50}$ | $EC_{50}$ | $SI^d$ |
|---|---|---|---|---|---|---|---|---|---|---|---|---|
| MC 507 | O | H | H | 2,5-Me₂-c-hex | H | H | H | H | H | 143 | 3.5 | 40 |
| MC 508 | O | H | H | 4,5-Me₂-c-hex | H | H | H | H | H | 58 | 6.4 | 9 |
| MC 512 | O | H | H | 3,5-Me₂-c-hex | H | H | H | H | H | >200 | 30 | >6.7 |
| MC 531 | O | Me | H | 2,5-Me₂-c-hex | H | H | H | H | H | 138 | 3.5 | 39 |
| MC 1114 | O | H | H | sec-but | F | H | H | H | F | 130 | 25 | 52 |
| MC 1103 | O | H | H | c-pent | F | H | H | H | F | >200 | 20 | >10 |
| MC 843 | S | H | H | Benzoyloxy-methyl | H | H | H | H | H | >200 | 45 | >4 |
| MC 796 | S | H | Ph | sec-but | H | H | H | H | H | 61 | >61 | — |
| MC 890 | S | H | Me | iso-prop | H | H | H | H | H | >200 | .9 | >222 |
| MC 892 | S | H | Me | c-pent | H | H | H | H | H | 159 | .6 | 333 |
| MC 898 | S | H | Me | c-hex | H | H | H | H | H | 149 | .6 | 248 |
| MC 899 | S | H | Et | iso-prop | H | H | H | H | H | 200 | .8 | 250 |
| MC 900 | S | H | Et | c-pent | H | H | H | H | H | >200 | 1.0 | >200 |
| MC 903 | S | H | Et | c-hex | H | H | H | H | H | >200 | 1.3 | >154 |
| MC 806 | S | H | H | sec-but | Me | H | H | H | H | >200 | 1.8 | >111 |
| MC 842 | S | H | H | c-pent | Me | H | H | H | H | >200 | 3.4 | >59 |
| MC 809 | S | H | H | sec-but | H | H | Me | H | H | 200 | 0.6 | 333.3 |
| MC 817 | S | H | H | sec-but | NO₂ | H | H | H | H | >200 | 0.25 | >800 |
| MC 897 | S | H | H | sec-but | H | NO₂ | H | H | H | 157 | 0.40 | 392 |
| MC 863 | S | H | H | sec-but | H | H | NO₂ | H | H | 151 | 1.5 | 101 |
| MC 854 | S | H | H | sec-but | Cl | H | H | H | H | 200 | 1 | 200 |
| MC 857 | S | H | H | sec-but | H | Cl | H | H | H | 116 | 2 | 58 |
| MC 859 | S | H | H | sec-but | H | H | Cl | H | H | 120 | 5 | 24 |
| MC 880 | S | H | H | sec-but | F | H | H | H | H | 200 | 0.26 | 769 |
| MC 884 | S | H | H | sec-but | H | F | H | H | H | >200 | 0.7 | >286 |
| MC 889 | S | H | H | sec-but | H | H | F | H | H | >200 | 8.7 | 23 |
| MC 825 | S | H | H | sec-but | NH₂ | H | H | H | H | >200 | 21.2 | >9 |
| MC 960 | S | H | H | sec-but | H | H | NH₂ | H | H | >200 | 23 | >8 |
| MC 868 | S | H | H | sec-but | CF₃ | H | H | H | H | >200 | 32 | 6.2 |
| MC 959 | S | H | H | sec-but | H | H | CF₃ | H | H | 200 | 25 | 8 |
| MC 952 | S | H | H | sec-but | OMe | H | H | H | H | >200 | 1.96 | >208 |
| MC 957 | S | H | H | sec-but | H | OMe | H | H | H | >200 | 1.2 | >166 |
| MC 964 | S | H | H | sec-but | H | H | OMe | H | H | 147 | 14 | 10.5 |
| MC 1041 | S | H | H | sec-but | H | F | H | F | H | >200 | 1.4 | >143 |
| MC 1042 | S | H | H | sec-but | H | Me | H | Me | H | 133 | 0.6 | 222 |
| MC 877 | S | H | H | Me | Cl | H | H | H | Cl | >200 | 3.2 | >62 |
| MC 878 | S | H | H | iso-prop | Cl | H | H | H | Cl | >200 | 1.9 | >105 |
| MC 886 | S | H | H | n-but | Cl | H | H | H | Cl | >200 | 0.44 | >454 |
| MC 885 | S | H | H | iso-but | Cl | H | H | H | Cl | >200 | 0.45 | >444 |
| MC 815 | S | H | H | sec-but | Cl | H | H | H | Cl | >200 | 0.14 | >1,428 |
| MC 888 | S | H | H | c-pent | Cl | H | H | H | Cl | >200 | 0.4 | >500 |
| MC 891 | S | H | H | c-hex | Cl | H | H | H | Cl | >200 | 0.6 | >333 |
| MC 871 | S | H | H | Me | F | H | H | H | F | 200 | 0.81 | 247 |
| MC 860 | S | H | H | iso-prop | F | H | H | H | F | >200 | 0.2 | >1,000 |
| MC 872 | S | H | H | n-but | F | H | H | H | F | 162 | 0.18 | 900 |
| MC 866 | S | H | H | iso-but | F | H | H | H | F | 182 | 0.14 | 1,300 |
| MC 848 | S | H | H | sec-but | F | H | H | H | F | 200 | 0.04 | 5,000 |
| MC 867 | S | H | H | c-pent | F | H | H | H | F | >200 | 0.08 | >2,500 |
| MC 870 | S | H | H | c-hex | F | H | H | H | F | 200 | 0.08 | 2,500 |
| MC 1001 | S | H | Me | iso-prop | Cl | H | H | H | Cl | 117 | 1.2 | 97.5 |
| MC 996 | S | H | Me | c-pent | Cl | H | H | H | Cl | 78.3 | 1.0 | 78.3 |
| MC 1016 | S | H | Me | c-hex | Cl | H | H | H | Cl | >200 | 2.9 | >69 |
| MC 1000 | S | H | Et | iso-prop | Cl | H | H | H | Cl | >200 | 0.4 | >500 |
| MC 1002 | S | H | Et | c-pent | Cl | H | H | H | Cl | 23.4 | 1.0 | 23.4 |
| MC 1003 | S | H | Et | c-hex | Cl | H | H | H | Cl | >200 | 3.6 | >55.5 |
| MC 1007 | S | H | Me | iso-prop | F | H | H | H | F | 167 | 0.05 | 3,340 |
| MC 1044 | S | H | Me | iso-but | F | H | H | H | F | >200 | 0.05 | >4,000 |
| MC 1045 | S | H | Me | n-but | F | H | H | H | F | >200 | 0.07 | 2,857 |
| MC 1110 | S | H | Me | sec-but | F | H | H | H | F | >200 | 0.03 | >6,666 |
| MC 1008 | S | H | Me | c-pent | F | H | H | H | F | >200 | 0.03 | >6,666 |
| MC 1013 | S | H | Me | c-hex | F | H | H | H | F | >200 | 0.16 | >1,250 |
| MC 1005 | S | H | Et | iso-prop | F | H | H | H | F | 70 | 0.08 | 875 |
| MC 1006 | S | H | Et | c-pent | F | H | H | H | F | 200 | 0.15 | 1,333 |
| MC 1014 | S | H | Et | c-hex | F | H | H | H | F | 130 | 0.05 | 2,600 |
| MC 971 | S | H | Me | iso-prop | CH=CH—CH=CH | | H | H | H | 119 | 1.1 | 108 |
| MC 972 | S | H | Me | c-pent | CH=CH—CH=CH | | H | H | H | 93 | 0.5 | 186 |
| MC 974 | S | H | Me | c-hex | CH=CH—CH=CH | | H | H | H | 45 | 0.14 | 321.4 |
| MC 969 | S | H | Et | iso-prop | CH=CH—CH=CH | | H | H | H | 50 | 1.5 | 33.3 |
| MC 973 | S | H | Et | c-pent | CH=CH—CH=CH | | H | H | H | 51 | 3.0 | 17 |
| MC 975 | S | H | Et | c-hex | CH=CH—CH=CH | | H | H | H | 16.9 | 0.18 | 94 |
| MC 844 | S | Me | H | sec-but | Me | H | H | H | H | >200 | 1.7 | >118 |
| MC 845 | S | Me | H | sec-but | H | H | Me | H | H | 26 | 0.8 | 32 |
| MC 925 | S | Me | H | sec-but | H | NO₂ | H | H | H | >200 | 0.35 | >571 |

TABLE 2-continued

Cytotoxicity and anti-HIV-1 Activity of MC Compounds.

| | | | | | | | | | | {μM} | | |
|---|---|---|---|---|---|---|---|---|---|---|---|---|
| Compd. | X | Y | Z | R | R¹ | R² | R³ | R⁴ | R⁵ | CC₅₀ | EC₅₀ | SI[d] |
| MC 924 | S | Me | H | sec-but | H | H | NO₂ | H | H | >200 | 2 | >100 |
| MC 909 | S | Me | H | sec-but | Cl | H | H | H | H | >200 | 0.27 | >741 |
| MC 910 | S | Me | H | sec-but | H | Cl | H | H | H | >200 | 0.96 | >208 |
| MC 911 | S | Me | H | sec-but | H | H | Cl | H | H | >200 | 9.5 | 20 |
| MC 913 | S | Me | H | sec-but | F | H | H | H | H | 140 | 0.41 | 341 |
| MC 918 | S | Me | H | sec-but | H | F | H | H | H | >200 | 1.2 | >166 |
| MC 919 | S | Me | H | sec-but | H | H | F | H | H | 105 | 11 | 9.5 |
| MC 912 | S | Me | H | Me | Cl | H | H | H | Cl | >200 | 3.2 | >62 |
| MC 914 | S | Me | H | iso-prop | Cl | H | H | H | Cl | >200 | 1.3 | >154 |
| MC 920 | S | Me | H | n-but | Cl | H | H | H | Cl | >200[e] | 1.17 | >171 |
| MC 916 | S | Me | H | iso-but | Cl | H | H | H | Cl | >200 | 1.2 | >166 |
| MC 850 | S | Me | H | sec-but | Cl | H | H | H | Cl | >200 | 0.05 | >4,000 |
| MC 915 | S | Me | H | c-pent | Cl | H | H | H | Cl | >200 | 1.8 | >111 |
| MC 917 | S | Me | H | c-hex | Cl | H | H | H | Cl | >200 | 22 | >9 |
| MC 869 | S | Me | H | Me | F | H | H | H | F | 200 | 0.19 | 1,053 |
| MC 881 | S | Me | H | iso-prop | F | H | H | H | F | >200 | 0.05 | >4,000 |
| MC 905 | S | Me | H | n-but | F | H | H | H | F | >200 | 0.08 | >2,500 |
| MC 921 | S | Me | H | iso-but | F | H | H | H | F | 64 | 0.1 | 640 |
| MC 849 | S | Me | H | sec-but | F | H | H | H | F | 80 | 0.001 | 8,000 |
| MC 922 | S | Me | H | c-pent | F | H | H | H | F | >200 | 0.08 | >2,500 |
| MC 923 | S | Me | H | c-hex | F | H | H | H | F | >200 | 0.09 | >2,222 |
| MC 1060 | S | Me | Me | Me | F | H | H | H | F | >200 | 0.04 | >5,000 |
| MC 1109 | S | Me | Me | sec-but | F | H | H | H | F | 200 | 0.03 | 6,666 |
| MC 1047 | S | Me | Me | c-pent | F | H | H | H | F | >200 | 0.009 | >22,222 |
| MC 798 | S | Et | H | sec-but | H | H | H | H | H | >200 | 1.0 | >200 |
| MC 1037 | S | Et | H | iso-prop | F | H | H | H | F | 65 | 0.2 | 326 |
| MC 1038 | S | Et | H | sec-but | F | H | H | H | F | >200 | 0.1 | >2,000 |
| MC 804 | S | Et | H | sec-but | CH=CH—CH=CH | | H | H | H | >200 | 5.3 | >34 |
| MC 1039 | S | iso-propyl | H | iso-prop | F | H | H | H | F | >200 | 0.4 | >500 |
| MC 852 | S | allyl | H | sec-but | H | H | H | H | H | >200 | 3 | >67 |
| MC 856 | S | n-prop | H | sec-but | H | H | H | H | H | 190 | 12 | 16 |
| MC 834 | S | n-but | H | sec-but | H | H | H | H | H | >200 | >200 | — |
| MC 1119 | NH | H | H | ethyl | F | H | H | H | F | >200 | 0.8 | >250 |
| MC 1078 | NH | H | H | n-prop | F | H | H | H | F | 200 | 0.11 | 1,818 |
| MC 979 | NH | H | H | iso-prop | F | H | H | H | F | >200 | 0.38 | >526 |
| MC 980 | NH | H | H | c-prop | F | H | H | H | F | >200 | 3.17 | >63 |
| MC 1077 | NH | H | H | n-but | F | H | H | H | F | 100 | 0.10 | 1,000 |
| MC 945 | NH | H | H | sec-but | F | H | H | H | F | >200 | 0.13 | >1,540 |
| MC 1043 | NH | H | H | MeOethyl | F | H | H | H | F | >200 | 0.8 | >250 |
| MC 1022 | NH | H | H | c-pent | F | H | H | H | F | >200 | 0.09 | >2,222 |
| MC 1049 | NH | H | H | c-hex | F | H | H | H | F | 66 | 0.14 | 471 |
| MC 1048 | NH | H | Me | c-pent | F | H | H | H | F | 75 | 0.03 | 2,500 |
| MC 1118 | NH | Me | H | iso-prop | F | H | H | H | F | 190 | 0.03 | 6,333 |
| MC 1130 | NH | Me | H | sec-but | F | H | H | H | F | 200 | 0.07 | 2,857 |
| MC 1050 | NH | Me | H | c-pent | F | H | H | H | F | >200 | 0.02 | >10,000 |
| MC 1105 | NH | Me | H | benzyl | F | H | H | H | F | 50 | 0.50 | 100 |
| MC 1129 | NH | Me | H | c-pent | F | H | H | H | F | 90 | 0.02 | 4,500 |
| MC 1167 | NH | H | H | Me | F | H | H | H | F | >200 | 1.5 | >133 |
| MC 1168 | NH | Me | H | Me | F | H | H | H | F | 135 | 0.4 | 335 |
| MC 1186 | NH | Me | H | n-prop | F | H | H | H | F | >200 | 0.02 | >10,000 |
| MC 1185 | NH | Me | H | n-but | F | H | H | H | F | >200 | 0.02 | >10,000 |
| MC 1178 | NH | H | Me | Me | F | H | H | H | F | 106 | 0.11 | 964 |
| MC 1190 | NH | H | Me | n-prop | F | H | H | H | F | 103 | 0.02 | 5,150 |
| MC 1191 | NH | H | Me | iso-prop | F | H | H | H | F | 115 | 0.03 | 3,830 |
| MC 1189 | NH | H | Me | n-but | F | H | H | H | F | 52 | 0.03 | 1,730 |
| MC 1192 | NH | H | Me | sec-but | F | H | H | H | F | 86 | 0.04 | 2,150 |
| MC 1180 | NH | H | Me | c-hex | F | H | H | H | F | 56 | 0.02 | 2,545 |
| MC 1170 | NH | Me | Me | Me | F | H | H | H | F | 200 | 0.03 | >6,666 |
| MC 1187 | NH | Me | Me | n-but | F | H | H | H | F | 83 | 0.01 | 8,300 |
| MC 1181 | NH | Me | Me | c-hex | F | H | H | H | F | 58 | 0.03 | 2,231 |
| MC 1182 | N | H | H | Me₂ | F | H | H | H | F | >200 | 0.05 | >4,000 |
| MC 1183 | N | H | H | Me-piperaz | F | H | H | H | F | >200 | 7.1 | >28 |
| MC 1188 | N | H | H | morph | F | H | H | H | F | >200 | 0.6 | >333 |
| MC 1193 | N | H | H | thiomorph | F | H | H | H | F | >200 | 0.05 | >4,000 |
| MC 1194 | N | H | H | piperid | F | H | H | H | F | >200 | 0.02 | >10,000 |
| MC 1196 | N | H | H | pyrrolid | F | H | H | H | F | >200 | 2.1 | >95 |
| MC 1202 | N | H | H | Et₂ | F | H | H | H | F | >200 | 0.26 | >769 |
| MC 1204 | N | H | H | (n-prop)₂ | F | H | H | H | F | >200 | 3.8 | >53 |
| MC 1195 | N | Me | H | Me₂ | F | H | H | H | F | >200 | 0.02 | >10,000 |
| MC 1203 | N | Me | H | Me-piperaz | F | H | H | H | F | >200 | 0.36 | >555 |
| MC 1205 | N | Me | H | morph | F | H | H | H | F | >200 | 0.047 | >4,255 |
| MC 1206 | N | Me | H | thiomorph | F | H | H | H | F | >200 | 0.09 | >2,222 |
| MC 1137 | S | Me | Me | iso-prop | F | H | H | H | F | 200 | 0.007 | 28,571 |

TABLE 2-continued

Cytotoxicity and anti-HIV-1 Activity of MC Compounds.

| Compd. | X | Y | Z | R | $R^1$ | $R^2$ | $R^3$ | $R^4$ | $R^5$ | $CC_{50}$ {μM} | $EC_{50}$ {μM} | $SI^d$ |
|---|---|---|---|---|---|---|---|---|---|---|---|---|
| MC 1175 | S | Me | Me | n-but | F | H | H | H | F | 112 | 0.008 | 14,000 |
| MC 1153 | S | Me | Me | iso-but | F | H | H | H | F | >200 | 0.01 | >20,000 |
| MC 1174 | S | Me | Me | c-hex | F | H | H | H | F | >200 | 0.018 | >11,111 |
| MC 1047+ | S | Me | Me | c-pent | F | H | H | H | F | >200 | 0.002 | >100,000 |
| MC 1047− | S | Me | Me | c-pent | F | H | H | H | F | >200 | 0.7 | >286 |
| MC 1161 | S | H | H | MeSMe | F | H | H | H | F | >200 | 0.80 | >250 |
| MC 1162 | S | Me | H | MeSMe | F | H | H | H | F | 30 | 0.12 | 250 |
| MC 1157 | S | Et | H | MeSMe | F | H | H | H | F | 50 | 0.11 | 454 |
| MC 1145 | S | iso-propyl | H | MeSMe | F | H | H | H | F | 200 | 0.10 | 2,000 |
| MC 1140 | S | H | H | MeSMe | H | H | H | H | H | >200 | 20 | >10 |

In another embodiment the invention provides compounds defined by the foregoing species, embodiments, and subembodiments.

Stereoisomerism and Polymorphism

The compounds of the present invention may have asymmetric centers and occur as racemates, racemic mixtures, individual diastereomers or enantiomers, with all isomeric forms being included in the present invention. Compounds of the present invention having a chiral center may exist in and be isolated in optically active and racemic forms. Some compounds may exhibit polymorphism. The present invention encompasses racemic, optically-active, polymorphic, or stereoisomeric form, or mixtures thereof, of a compound of the invention, which possess the useful properties described herein. The optically active forms can be prepared by, for example, resolution of the racemic form by recrystallization techniques, by synthesis from optically-active starting materials, by chiral synthesis, or by chromatographic separation using a chiral stationary phase or by enzymatic resolution.

Opitically active forms of the compounds can be prepared using any method known in the art, including by resolution of the racemic form by recrystallization techniques, by synthesis from optically-active starting materials, by chiral synthesis, or by chromatographic separation using a chiral stationary phase.

Examples of methods to obtain optically active materials include at least the following.

i) physical separation of crystals—a technique whereby macroscopic crystals of the individual enantiomers are manually separated. This technique can be used if crystals of the separate enantiomers exist, i.e., the material is a conglomerate, and the crystals are visually distinct;

ii) simultaneous crystallization—a technique whereby the individual enantiomers are separately crystallized from a solution of the racemate, possible only if the latter is a conglomerate in the solid state;

iii) enzymatic resolutions—a technique whereby partial or complete separation of a racemate by virtue of differing rates of reaction for the enantiomers with an enzyme;

iv) enzymatic asymmetric synthesis—a synthetic technique whereby at least one step of the synthesis uses an enzymatic reaction to obtain an enantiomerically pure or enriched synthetic precursor of the desired enantiomer;

v) chemical asymmetric synthesis—a synthetic technique whereby the desired enantiomer is synthesized from an achiral precursor under conditions that produce asymmetry (i.e., chirality) in the product, which may be achieved using chiral catalysts or chiral auxiliaries;

vi) diastereomer separations—a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations—a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

viii) kinetic resolutions—this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors—a synthetic technique whereby the desired enantiomer is obtained from non-chiral starting materials and where the stereochemical integrity is not or is only minimally compromised over the course of the synthesis;

x) chiral liquid chromatography—a technique whereby the enantiomers of a racemate are separated in a liquid mobile phase by virtue of their differing interactions with a stationary phase (including via chiral HPLC). The stationary phase can be made of chiral material or the mobile phase can contain an additional chiral material to provoke the differing interactions;

xi) chiral gas chromatography—a technique whereby the racemate is volatilized and enantiomers are separated by virtue of their differing interactions in the gaseous mobile phase with a column containing a fixed non-racemic chiral adsorbent phase;

xii) extraction with chiral solvents—a technique whereby the enantiomers are separated by virtue of preferential dissolution of one enantiomer into a particular chiral solvent;

xiii) transport across chiral membranes—a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane that allows only one enantiomer of the racemate to pass through.

Chiral chromatography, including simulated moving bed chromatography, is used in one embodiment. A wide variety of chiral stationary phases are commercially available.

Definitions

When any variable occurs more than one time in any constituent or in formula A of this invention, its definition on each occurrence is independent of its definition at every other occurrence. Also, combinations of substituents and/or variables are permissible only if such combinations result in stable compounds.

As used herein except where noted, "alkyl" is intended to include both branched- and straight-chain saturated aliphatic hydrocarbon groups having the specified number of carbon atoms; "Halogen" or "Hal" as used herein, means fluoro, chloro, bromo and iodo.

As used herein, with exceptions as noted, "aryl" is intended to mean any stable monocyclic, bicyclic or tricyclic carbon ring of up to 7 members in each ring, wherein at least one ring is aromatic as defined by the Huckel 4n+2 rule. Examples of aryl ring systems include phenyl, naphthyl, tetrahydronaphthyl, biphenyl.

The term heterocycle or heterocyclic, as used herein except where noted represents a stable 5- to 7-membered monocyclic or stable 8- to 11-membered bicyclic heterocyclic ring which is either saturated or unsaturated, and which consists of carbon atoms and from one to three heteroatoms selected from the group consisting of N, O and S; and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure.

The pharmaceutically-acceptable salts of the compounds of this invention that are capable of salt formation (in the form of water- or oil- soluble or dispersible products) include the conventional non-toxic salts or the quaternary ammonium salts of these compounds, which are formed, e.g., from inorganic or organic acids or bases.

Secondary Antiviral Constituents

The compositions of this invention may optionally contain a second anti-HIV agent. Exemplary agents include AZT, D4T, FTC (2',3'-dideoxy-3'-thia-5-fluorocytidine); 3TC (Epivir, Glaxo Wellcome, Inc.), AZDU (3'-Azido-2',3'-dideoxyuridine); 141W94 (amprenavir, GlaxoWellcome, Inc.); Viramune (nevirapine), Rescriptor (delavirdine); or DMP-266 (efavirenz). Other examples of anti-HIV agents include DDI, DDC, Delaviridine, β-LddA, β-L-3'-azido-d5FC, carbovir, acyclovir, interferon, stavudine, CS-92 (3'-azido-2',3'-dideoxy-5-methyl-cytidine), 3'-azido nucleosides, and β-D-dioxolane nucleosides such as β-D-dioxolanylguanine (DXG), β-D-dioxolanyl-2,6-diarninopurine (DAPD), and β-D-dioxolanyl-6-chloropurine (ACP).

Preferred protease inhibitors include indinavir ({1(1,S, 2R),5(S)}-2,3,5-trideoxy-N-(2,3-dihydro-2-hydroxy-1H-inden-1-yl)-5-{2-{{(1,1-dimethylethyl)amino}carbonyl}-4-(3-pyridinylmethyl)-1-piperazinyl}-2-(phenylmethyl)-D-erythro-pentoamide sulfate; Merck), nelfinavir (Agouron), ritonavir (Abbot), and saquinavir (Invirase; Roche).

Nonliniting examples of other compounds that can be administered in combination or alternation with the compounds of the present invention to augment the properties of the drug on administration include abacavir: (1S,4R)-4-{2-amino-6-cyclopropyl-amino)-9H-purin-9-yl}-2-cyclopentene-1-methanol succinate (1592U89, a carbovir analog; Glaxo Wellcome); zidovudine: AZT, 3'-azido-3'-deoxythymidine (Glaxo Wellcome); BILA 1906: N-{1S-{{{3-{2S-{(1,1-dimethylethyl)amino}carbonyl}-4R-}-3-pyridinylmethyl)-thio}-1-piperidinyl}-2R-hydroxy-1S-(phenyhnethyl)propyl}amino}carbonyl}-2-methylpropyl}-2-quinolinecarboxamide (Bio Mega/Boehringer-Ingelheim); BILA 2185: N-(1,1-dimethylethyl)-1-{2S-{{2-2,6-dimethylphenoxy)-1-oxoethyl}amino}-2R-hydroxy-4-phenylbutyl}4R-pyridinylthio)-2-piperidinecarboxamide (Bio Mega/Boehringer-Ingelheim); BM+51.0836:triazoloisoindolinone derivative; BMS 186, 318: aminodiol derivative HIV-1 protease inhibitor (Bristol-Myers-Squibb); d4API: 9-{2,5-dihydro-5-(phosphonomethoxy)-2-furanel}adenine (Gilead); stavudine: d4T, 2',3'-didehydro-3'-deoxythymidine (Bristol-Myers-Squibb); efavirenz: DMP-266, a 1,4-dihydro-2H-3, 1-benzoxazin-2-one; HBY097: S-4-isopropoxycarbonyl-6-methoxy-3-(methylthiomethyl)-3,4-dihydroquinoxalin-2 (1H)-thione; HEPT: 1-{(2-hydroxyethoxy)methyl}6-(phenylthio)-thymine; KNI-272: (2S,3S)-3-amino-2-hydroxy-4-phenylbutyric acid-containing tripeptide; L-697, 593; 5-ethyl-6-methyl-3-(2-phthalimido-ethyl)pyridin-2 (1H)-one; L-735,524: hydroxy-aminopentane amide HIV-1 protease inhibitor (Merck); L-697,661: 3-{ {(−4,7-dichloro-1,3-benzoxazol-2-yl)methyl}amino}-5-ethyl-6-methylpyridin-2(1H)-one; L-FDDC: (−)-β-L-5-fluoro-2',3'-dideoxycytidine; L-FDOC: (−)-β-L-5-fluoro-dioxolane cytosine; 6-benzyl-1-ethoxymethyl-5-isopropyluracil (I-EBU; Triangle/Mitsubishi); nevirapine: 11-cyclopropyl-5,11-dihydro-4-methyl-6H-dipyridol{3,2-b:2',3'-e}diazepin-6-one (Boehringer-Ingelheim); PFA: phosphonoformate (foscarnet; Astra); PMEA: 9-(2-phosphonylmethoxyethyl) adenine (Gilead); PMPA: (R)-9-(2-phosphonyl-methoxypropyl)adenine (Gilead); Ro 31-8959: hydroxythethylamine derivative HIV-1 protease inhibitor (Roche); RPI-3121: peptidyl protease inhibitor, 1-{(3s)-3-(n-alpha-benzyloxycarbonyl)-1-asparginyl)-amino-2-hydroxy-4-phenylbutyryl}-n-tert-butyl-1-proline amide; 2720: 6-chloro-3,3-dimethyl-4-(isopropenyloxycarbonyl)-3,4-dihydro-quinoxalin-2(1H) thione; SC-52151: hydroxyethylurea isostere protease inhibitor (Searle); SC-55389A: hydroxyethyl-urea isostere protease inhibitor (Searle); TIBO R82150: (+)-(5S)-4,5,6,7-tetrahydro-5-methyl-6-(3-methyl-2-butenyl)imidazo {4,5, 1jk}-{1,4}-benzodiazepin-2(1H)-thione (Janssen); TIBO 82913: (+)-(5S)-4,5,6,7,-tetrahydro-9-chloro-5-methyl-6-(3-methyl-2-butenyl)imidazo {4,5,1jk}-{1, 4}benzodiazepin-2(1H)-thione (Janssen); TSAO-m3T: {2',5'-bis-O-(tert-butyldimethylsilyl)-3 '-spiro-5 '-(4'-amino-1,'2'-oxathiole-2',2'-dioxide)}-β-D-pentofuranosyl-N3-methylthymine; U90152: 1-{3-{(1-methylethyl)-amino}2-pyridinyl}-4-{{5-{(methylsulphonyl)-amino}-11H-indol- 2yl}carbonyl}piperazine; UC: thiocarboxanilide derivatives (Uniroyal); UC-781 =N-{4-chloro-3-(3-methyl-2-butenyloxy)phenyl}-2-methyl-3-furancarbothioamide; UC-82 =N-{4-chloro-3-(3-methyl-2-butenyloxy)phenyl}-2-methyl-3-thiophenecarbothioamide; VB 11,328: hydroxyethylsulphonamide protease inhibitor (Vertex); VX-478: amprenavir, 141W94, hydroxyethylsulphonamide protease inhibitor (Vertex/Glaxo Wellcome); XM 323: cyclic urea protease inhibitor (Dupont Merck), delaviridine (Pharmacia Upjohn), famciclovir, gancyclovir, and penciclovir.

In one embodiment, a compound of the present invention is administered in combination with LG1350, which has the following structure.

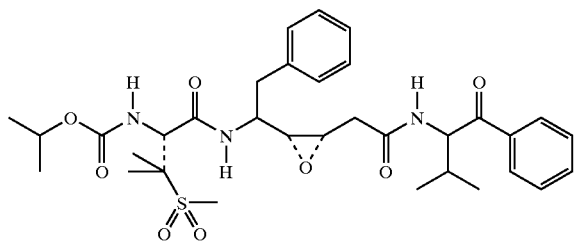

Synthetic Methods

Preparation of compounds of formula (1) can be achieved by the general procedures listed below.

SCHEME A

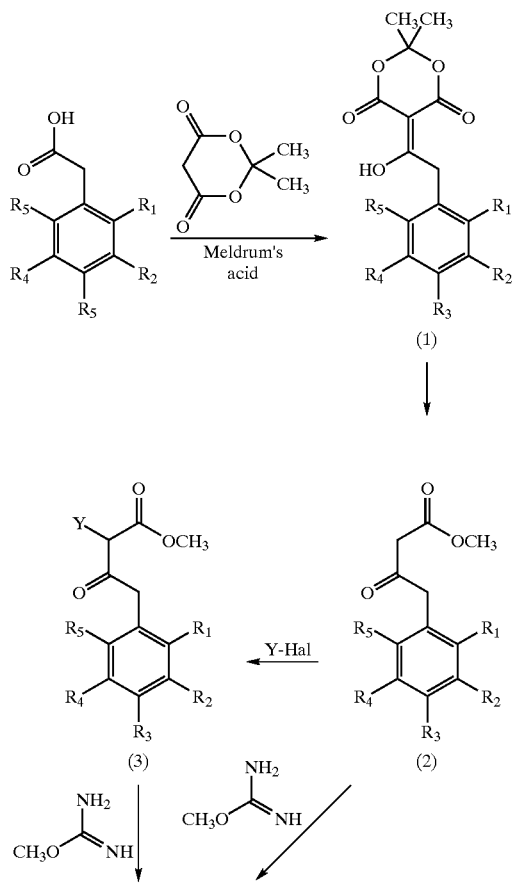

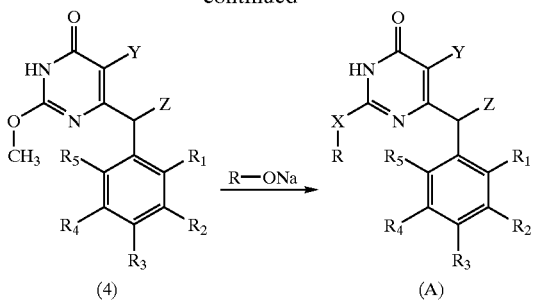

Anhydrous pyridine (400 mmoles, 32.5 ml) was added with stirring under nitrogen atmosphere into an ice-cooled solution of 2,2-dimethyl-1,3-dioxane-4,6-dione (Meldrurm's acid) (165 mmoles, 23.75 g) in anhydrous dichloromethane (50 ml). The resulting solution was treated, over a 2 h period at 0° C. under nitrogen atmosphere, with a solution of crude arylacetyl chloride in anhydrous dichloromethane (50 ml). Arylacetyl chloride was prepared before use by refluxing the proper arylacetic acid (43.2 mmoles) with thionyl chloride (21.3 ml) under nitrogen atmosphere for 2 h. Then, the mixture was stirred for 2 h at room temperature, poured into crushed ice and treated with 2N HCl (100 ml). The organic layer was separated and the aqueous solution was extracted twice with dichloromethane (25 ml). The organic phase and the extracts were combined, washed with brine, dried and evaporated. The solid residue was dissolved in anhydrous methanol (250 ml) and the solution was refluxed for 20 h. After cooling, metal sodium (0.16 g-atoms, 3.68 g) was carefully added and the mixture was stirred until dissolution was complete. Alkyl halide (160 mmoles) was dropped into the solution and the resulting mixture was heated at reflux for 4–12 h. After cooling, the solvent was removed and the residue treated with water (200 ml) and extracted with chloroform (3×100 ml). The organic layer was washed with brine (2×100 ml), dried and evaporated to give the desired compound (3), which was purified by passing through a silica gel column (chloroform as eluent).

In the above reaction, arylacetic acid (Scheme "A") or arylacetyl chloride can be replaced with the corresponding 1-arylacetylimidazolide (Scheme "B") or with arylacetylethoxycarbonylanhydride, whereas the Meldrum's acid can be replaced with ethyl acetylacetate, ethyl alkylmalonate or ethyl alkylmalonate potassium salt, to give the proper ethyl arylacetylalkylacetates in high yields.

Preparation Of Compounds (I) (in Scheme B) with X=O (See Scheme A).

The proper methyl arylacetylalkylacetate (2) (10 mmoles) in methanol (50 ml) was added to a well-stirred suspension of O-methylisourea hydrogen sulphate (15 mmoles, 2.58 g) and calcium hydroxide (16 mmoles, 1.18 g) in water (50 ml). The resulting mixture was stirred at room temperature for 72 h, then concentrated, made acid (pH 5) with 0.5N acetic acid and extracted with ethyl acetate (3×50 ml). The combined organic extracts were washed with brine (100 ml), dried and evaporated to dryness. The residue was purified by crystallization from the proper solvent yielding pure 5-alkyl-6-benzyl-3,4-dihydro-2-methoxypyrimidin-4-one (4). This compound was then refluxed with the proper potassium alkoxide (100 mmoles of potassium metal in 20–30 ml of alcohol freshly distilled on sodium metal) under nitrogen atmosphere until starting material disappeared at the TLC control. After cooling, the mixture was concentrated, made acid (pH 5) with 0.5N acetic acid and extracted with ethyl acetate (3×50 ml). The combined extracts were washed once with brine (100 ml), dried and evaporated to give the required 2-alkoxy-5-alkyl-6-benzyl-3,4-dihydropyrimidin-4-one derivative (A), which was recrystallized from a suitable solvent or purified by column chromatography (silica gel; ethyl acetate:chloroform 1:1). Physical and chemical data of representative compounds of the invention are reported in table 1; cytotoxicity and anti-HIV-1 activity data are reported in table 2.

The proper ethyl arylacetylalkylacetate (31.5 mmoles) was successively added to a stirred solution of sodium metal (0.063 g-atoms) in 50 mL of absolute ethanol (50 ml) and thiourea (43 mmoles). The mixture was heated while stirring at reflux for 5 h. After cooling, the solvent was distilled in vacuo at 40–50° C. until dryness and the residue was dissolved in water (200 mL) and made acid (pH 5) with 0.5N acetic acid. The resulting precipitate (the crude 2-thiouracil derivative) was filtered under reduced pressure, washed with diethyl ether, vacuum dried at 80° C. for 12 h and then crystallized from the proper solvent (I).

Then, according to method A, iodomethane (8 mmoles, 1.13 g) was added to a suspension containing the proper

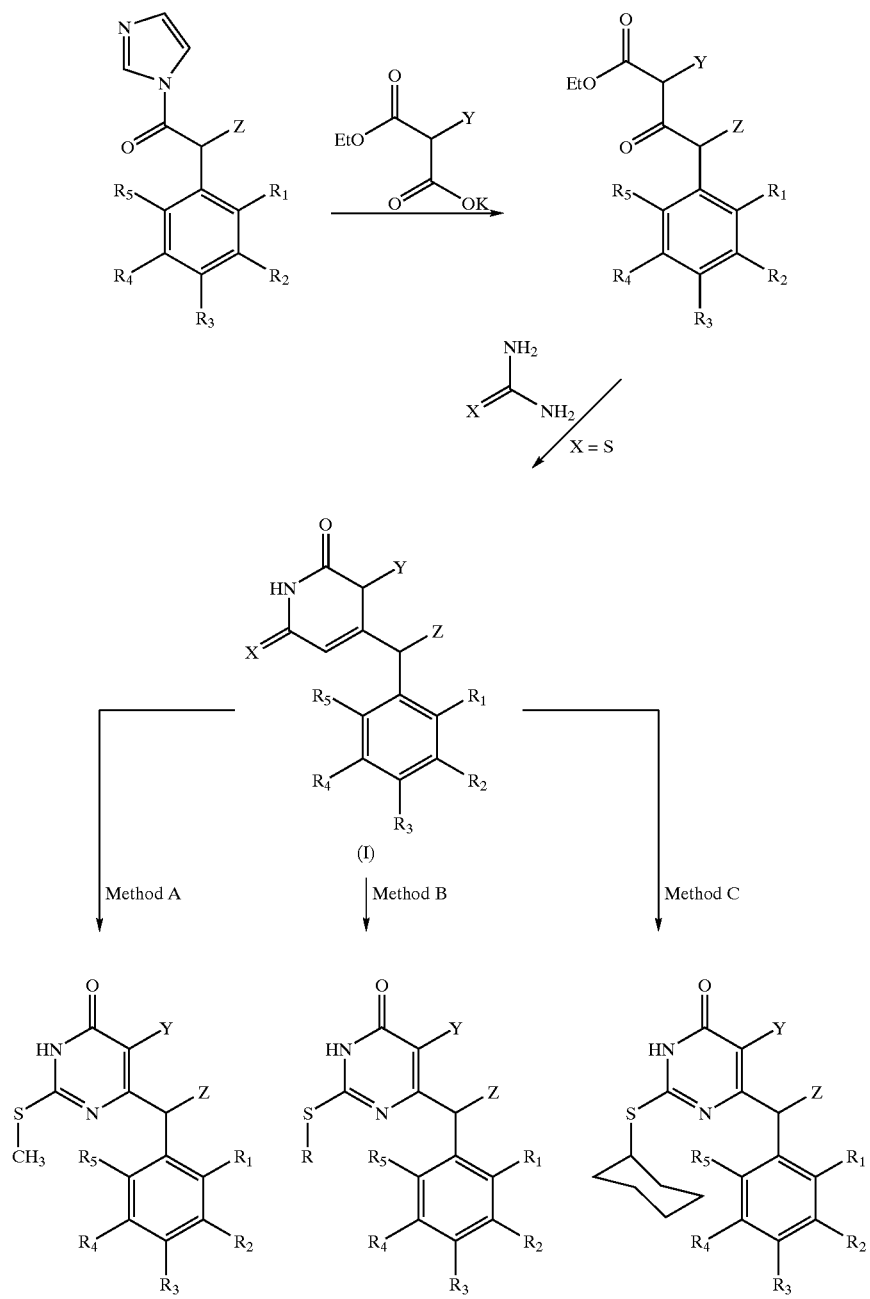

2-thiouracil derivative (4 mmoles) in anhydrous N,N-dimethylformamide (2 ml), and the resulting mixture was stirred at room temperature until the starting material disappeared at the TLC control (silica gel; n-hexane: ethyl acetate: methanol 12:3:1). Then the reaction content was poured on cold water (100 mL) and extracted with ethyl acetate (3×50 ml). The organic layers were collected, washed with a sodium thiosulfate solution (100 ml), brine (3×50 ml), dried and evaporated to furnish the crude 5-alkyl-6-benzyl-3,4-dihydro-2-methylthiopyrimidin-4-one (5) as a solid purified by crystallization.

Alternatively, according to methods B and C, potassium carbonate (4.2 mmoles) and the proper alkyl halide (4.4 mmoles) were added to a suspension containing 2-thiouracil derivative (4 mmoles) in anhydrous N,N-dimethylformamide (2 ml). The resulting mixture was stirred at room temperature (method B) or at 80° C. (method C) until starting material disappeared at the TLC control (silica gel; n-hexane:ethyl acetate:methanol 12:3:1). Then the reaction content was poured on cold water (200 mL), made acid (pH 5) with 0.5N acetic acid and extracted with ethyl acetate (3×50 ml). The organic layers were collected, washed with a sodium thiosulfate solution (100 ml), brine (100 ml), dried and evaporated to furnish 5-alkyl-6-benzyl-3,4-dihydro-2-methylthiopyrimidin-4-ones (6) and (7) as crude material which was then purified by column chromatography on silica gel (eluent: n-hexane:ethyl acetate:methanol 12:3:1) followed by crystallization. Physical and chemical data of representative compounds of the invention are reported in table 1. Cytotoxicity and anti-HIV-1 activity in vitro are reported in table 2.

SCHEME C

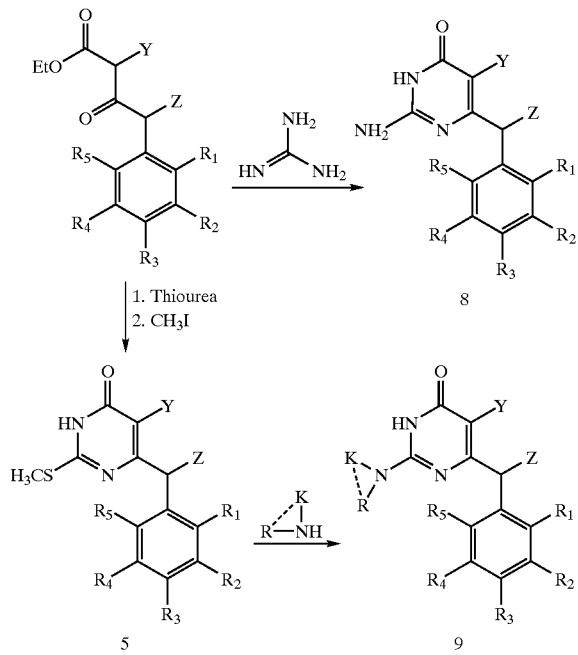

Title derivatives were prepared according to the procedure described for the synthesis of compounds with X=S (I), using ethyl arylacetylalkylacetates and guanidine {2-amino-6-benzylpyrimidin-4-ones (8)} as starting materials. 2-Alkylaminoderivatives (9) were synthesized by heating the previously reported 5-alkyl-6-benzyl-3,4-dihydro-2-methylthio pyrimidin-4-ones with 20–30 ml of proper amine in a sealed tube at 170° C. for 24 h. Physical and chemical data of some compounds (9) are reported in table 1. Cytotoxicity and anti-HIV-1 activity in vitro are reported in table 2.

Assay Procedures for Results Reported in Tables 1 and 2

Compounds. Compounds were solubilized in DMSO at 200 mM and then diluted into culture medium.

Cells and viruses. MT-4, C8166,H9/IIIB and CEM cells were grown at 37° C. in a 5% $CO_2$ atmosphere in RPMI 1640 medium, supplemented with 10% fetal calf serum (FCS), 100 IU/mL penicillin and 100 µg/mL streptomycin. Cell cultures were checked periodically for the absence of mycoplasma contamination with a MycoTect Kit (Gibco). Human immunodeficiency virus type-I (HIV-1, $III_B$ strain) was obtained from supernatants of persistently infected H9/$III_B$ cells. HIV-1 stock solution had a titres of $4.5 \times 10^6$ 50% cell culture infectious dose ($CCID_{50}$)/ml.

HIV Titration. Titration of HIV was performed in C8166 cells by the standard limiting dilution method (dilution 1:2, four replica wells per dilution) in 96-well plates. The infectious virus titre was determined by light microscope scoring of cytopathicity after 4 days of incubation and the virus titres were expressed as $CCID_{50}$/mL.

Anti-HIV Assays. Activity of the compounds against HIV-1 and HIV-2 multiplication in acutely infected cells was based on the inhibition of virus-induced cytopathicity in MT-4 and C8166 cells, respectively. Briefly, 50 µL of culture medium containing $1 \times 10^4$ cells were added to each well of flat-bottom microtiter trays containing 50 µl of culture medium with or without various concentrations of the test compounds. Then 20 µL of an HIV suspension containing 100 $CCID_{50}$ were added. After a 4-day incubation at 37° C., the number of viable cells was determined by the 3-(4,5-dimethylthiazol-1-yl)-2,5-diphenyltetrazolium bromide (MTT) method. Cytotoxicity of the compounds was evaluated in parallel with their antiviral activity. It was based on the viability of mock-infected cells, as monitored by the MTT method.

RT Assays. Assays were performed as follows. Briefly, purified rRT was assayed for its RNA-dependent polymerase-associated activity in a 50 µL volume containing: 50 mM TrisHCl (pH 7.8), 80 mM KCl1, 6 mM MgCl2, 1 mM DTT, 0.1 mg/mL BSA, 0.3 $OD_{260}$ unit/mL template:primer {poly(rC)-oligo(dG)12–18} and 10 µM {$^3$H}dGTP (1 Ci/mmol). After incubation for 30 min at 37° C., the samples were spotted on glass fiber filters (Whatman GF/A), and the acid-insoluble radioactivity was determined.

EXAMPLES

Example 1

2-Cyclopentylthio-6-(2,6-difluorophenylmethyl)-3,4-dihydrogyrimidin-4-(3H)-one (MC867)

A mixture of 6-(2,6-difluorophenylmethyl)-1,2,3,4-tetrahydro-2-thiopyrimidin-4(3H)-one (0.16 g, 0.65 mmol; prepared as reported in scheme B), cyclopentyl bromide (0.11 g, 0.08 mL., 0.71 mmol) and potassium carbonate (0.09 g, 0.65 mmol) in 1 mL of anhydrous DMF was stirred at room temperature for 24 h. After treatment with cold water (200 mL), the solution was extracted with ethyl acetate (3×50 mL). The organic layers were collected, washed with brine (3×50 mL), dried and evaporated to furnish crude MC867, which was purified by chromatography on silica gel column (eluent: n-hexane/ethyl acetate/methanol 12/3/1).

Yield (%): 45; mp (° C.): 168–169; recrystallization solvent: cyclohexane; formula (molecula-weight): $C_{16}H_{16}F_2N_2OS$ (322.37).

Example 2

2-Cyclopenlylthio-6-(2,6-difluorophenylmethyl)-3,4-dihydro-5-methylpyrimidin-4-(3H)-one (MC922)

The synthesis of MC922 was accomplished according to the above reported procedure starting from 6-(2,6-difluorophenylmethyl)-5-methyl-1,2,3,4-tetrahydro-2-thiopyrimidin-4-(3H)-one (see scheme B).

Yield (%): 54; mp (° C.): 192–193; recrystallization solvent: cyclohexane; formula (molecular weight): $C_{17}H_{18}F_2N_2OS$ (336.40).

Example 3

2-Cyclopentylthio-6-{1-(2,6-difluorophenyl)ethyl}-3,4-dihydropyrimidin-4-(3H)-one (MC1008)

The synthesis of MC1008 was accomplished according to the above reported procedure starting from 6-{1-(2,6-difluorophenyl)ethyl}-1,2,3,4-tetrahydro-2-thiopyrimidin-4(3H)-one (see scheme B).

Yield (%): 54; mp (° C.): 165.5—166.5; recrystallization solvent: cyclohexane; formula (molecular weight): $C_{17}H_{18}F_2N_2OS$ (336.40).

Example 4

2-Cyclopentylthio-6-{1-(2,6-difluorophenyl)ethyl}-3,4-dihydro-5-methylpyrimidin-4(3H)-one (MC 1047)

The synthesis of MC1047 was accomplished according to the above reported procedure, starting from 6-{1-(2,6-difluorophenyl)ethyl}-5-methyl-1,2,3,4-tetrahydro-2-thiopyrimidin-4(3H)-one (see scheme B).

Yield (%): 60; mp (° C.): 196–197; recrystallization solvent: cyclohexane; formula (molecular weight): $C_{18}H_{20}F_2N_2OS$ (350.43).

Example 5

6-(2,6-Difluorophenyhnethyl)-3,4-dihydro-2-(methylthiomethyl)thiopyrimidin-4-(3H)-one (MC 1161)

The synthesis of MC1161 was accomplished according to the above reported procedures, starting from 6-(2,6-difluorophenylmethyl)-1,2,3,4-tetrahydro-2-thiopyrimidin-4(3H)-one (see scheme B) and chloromethyl methyl sulfide.

Yield (%): 72; mp (° C.): 159–160; recrystallization solvent: benzene/cyclohexane; formula (molecular weight): $C_{13}H_{12}F_2N_2OS_2$ (314.37)

Example 6

6-(2,6-Difluorophenylmethyl)-3,4-dihydro-5-methyl-2-(methylthiomethyl)thiopyrimidin-4(3H)-one (MC 1162)

The synthesis of MC1162 was accomplished according to the above reported procedure, starting from 6-(2,6-difluorophenylmethyl)-5-methyl-1,2,3,4-tetrahydro-2-thiopyrimidin 4(3H)-one (see scheme B) and chloromethyl methyl sulfide.

Yield (%): 70; mp (° C.): 183–184; recrystallization solvent: benzene/cyclohexane; formula (molecular weight): $C_{14}H_{14}F_2N_2OS_2$ (328.39).

Example 7

6-(2,6-Difluorophenyhnethyl)-3,4-dihydro-5-(1-methylethyl)-2-(methylthiomethyl) thiopyrimidin-4-(3H)-one MC 1145)

The synthesis of MC1145 was accomplished according to the above reported procedure, starting from 6-(2,6-difluorophenylmethyl)-5-(1-methylethyl)-1,2,3,4-tetrahydro-2-thiopyrimidin-4(3H)-one (see scheme B) and chloromethyl methyl sulfide.

Yield (%): 62; mp (° C.): 158.5–160; recrystallization solvent: cyclohexane; formula (molecular weight): $C_{16}H_{18}F_2N_2OS_2$ (356.45).

Example 8

2-Cyclopenltylamino-6-(2,6-difluorophenylmethyl)-3,4-dihydropyrimidin-4-(3H)-one (MC1022)

Cyclopentylamine (10 mL) was heated while stirring with 6-(2,6-difluorophenylmethyl)-3,4-dihydro-2-methylthiopyrimidin-4(3H)-one (0.30 g, 1.12 mmol; prepared as reported in scheme B or C) in a sealed tube at 160° C. for 10 h. After cooling, the mixture was diluted with water (200 mL) and extracted with ethyl acetate (3×50 mL). The organic layers were collected, washed with brine (3×50 mL), dried and evaporated to furnish crude MC1022, which was purified by chromatography on silica get column (eluent: ethyl acetate/chloroform 1/1).

Yield (%): 74; mp (° C.):-(oil); formula (molecular weight): $C_{16}H_{17}F_2N_3O$ (305.33).

Example 9

2-Cyclopentylamino-6-(2,6-difluorophenylmethyl)-3,4-dihydro-5-methylpyrimidin-4-(3H)-one (MC1050)

The synthesis of MC1050 was accomplished according to the above reported procedure, starting from 6-(2,6-difluorophenylmethyl)-3,4-dihydro-5-methyl-2-methylthiopyrimidirin-4(3H)-one (see scheme B or C).

Yield (%): 60; mp (° C.): 115–117; recrystallization solvent: n-hexane/cyclohexane; formula (molecular weight): $C_{17}H_{19}F_2N_3O$ (319.35).

Example 10

2-Cyclopentylamino-6-{1-(2,6-difluorophenyl)ethyl}-3,4-dihydropyrimidin-4-(3H)-one (MC1048)

The synthesis of MC1048 was accomplished according to the above reported procedure, starting from 6-{1-(2,6-difluorophenyl)ethyl}-3,4-dihydro-2-methylthiopyrimidin-4(3H)-one (see scheme B or C).

Yield (%): 48; mp (° C.):-(oil); formula (molecular weight): $C_{17}H_{19}F_2N_3O$ (319.35).

Example 11

2-Cyclopentylamino-6-{1-(2,6-difluorophenyl)ethyl}-3,4-dihydro-5-methylpyrimidin-4-(3H)-one (MC1129)

The synthesis of MC 1129 was accomplished according to the above reported procedure, starting from 6-{1-(2,6-difluorophenyl)ethyl}-3,4-dihydro-5-methyl-2-methylthiopyrimidin-4(3H)-one (see scheme B or C).

Yield (%): 38; mp (° C.):-(oil); formula (molecular weight): $C_{18}H_{21}F_2N_3O$ (333.38).

Example 12

6-(2,6-Difluorophenylmethyl)-3,4-dihydro-2-(4-thiomorpholin-1-yl)-pyrimidin-4-(3H)-one (MC1193)

The synthesis of MC1193 was accomplished according to the above reported procedure, starting from thiomorpholine and 6-(2,6-difluorophenylmethyl)-3,4-dihydro-2-methylthiopyrimidin-4(3H)-one (see scheme B or C).

Yield (%): 78; mp (° C.): 233–234; recrystallization solvent: acetonitrile; formula (molecular weight): $C_{15}H_{15}F_2N_3OS$ (323.36).

Example 13

6-(2,6-Difluorophenylmethyl)-3,4-dihydro-2-N,N-dimethylaminopyrimidin-4-(3H)-one (MC 1182)

To a stirred solution of sodium metal (0.14 g, 6.3 mg-atoms) in absolute ethanol (50 mL) 1,1-dimethylguanidine sulfate (1.17 g, 4.3 mmol) and ethyl 4-(2,6-difluorophenyl)acetylacetate (0.76 g, 3.15 mmol) were successively added. The mixture was heated while stirring at reflux for 8 h. After cooling, the solvent was distilled in vacuo at 40–50° C. until dryness and the residue was dissolved in water (200 mL) and made acid (pH 5) with 0.5N acetic acid. The resulting precipitate (the crude isocytosine derivative) was filtered under reduced pressure, washed with diethyl ether, vacuum dried at 80° C. for 12 h and then crystallized from benzene/cyclohexane (see scheme C starting from ethyl 4-(2,6-difluorophenyl)acetylacetate and replacing guanidine hydrochloride with 1,1-dimethylguanidine sulfate).

Yield (%): 88; mp (° C.): 210–211; recrystallization solvent: benzene/cyclohexane; formula (molecular weight): $C_{13}H_{13}F_2N_3O$ (265.26).

Examples 14–16

Evaluation of Longevity of Protection from HIV

Compounds of the present invention were assayed for length of HIV protection using the following methods:
Cells.

To evaluate the antiviral activity of test compounds the following cell types were used: T lymphocytes (PBLs) and monocytes from peripheral blood of healthy donors; U937, human monocyte cell line permissive for HIV replication; C8166 and MT-4, human $CD^{4+}$ T-cell lines permissive for HIV replication; H9, human CD4+ T-cell line permissive for HIV replication, but partially resistant to its cytopathic effect; H9/IIIB, subclone of H9 cells chronically infected with HIV-1 (strain IIIB). Cytotoxicity was evaluated in the above cell types and also in primary cultures of fibroblasts and in HeLa and ME-180 cell lines, which originated from human cervix. Cells were grown in RPMI-1640 (H9, MT-4, C8166, U937, PBMC, PBL) or in DMEM (HeLa, ME-180, fibroblasts) medium supplemented with 10% FCS, 100 units/mL penicillin and 100 µg/mL streptomycin. The cultures were incubated at 37° C. in a humidified, 5% $CO_2$ atmosphere. The absence of mycoplasma contamination was periodically checked by the Hoechst staining method.
Virus.

HIV-1(strains IIIB, NM, RF, Ba-L) and HIV-2 (ROD strain) were obtained from the supernatant of persistently infected cells. The CBL-20 strain of HIV-2, kindly obtained from "MRC AIDS Directed Program Reagent Project", was propagated in MT-4 cells. Clinical isolates of HIV-1 from peripheral blood and from seminal fluid, were propagated in PBLs. The HIV stock solutions were titrated in C8166 cells and kept at −80° C. until use.
Cytotoxicity Assays.

Cells were resuspended in growth medium at a density of $1\times10^5$/mL and incubated in the absence or in the presence of various concentrations of test compounds. Cell numbers at each concentration were determined in a Coulter counter after 72–96 hours at 37° C. The percentage of viable cells at each concentration was determined by the Trypan blue dye exclusion method or, alternatively, by the MTT method (see below).
P24 Assay.

The levels of p24 viral protein were determined in the cell-free culture supernatants by the HIV-1 p24 antigen enzyme-linked immunosorbent assay kit (ELISA, Abbott).
Evaluation of Long-Term Cytotoxicity.

MT-4 cells, seeded at $1\times10^5$/mL in growth medium, were incubated in the absence or in the presence of various concentrations of the test compounds, alone or in combination. Every 3–4 days, in order to bring cells back to the initial conditions of low density and allow continuous exponential growth, the cultures were diluted in fresh medium containing or not the same concentrations of the test compounds. Cell viability was determined at each sub-cultivation stage by the MTT method.
MTT Method.

Due to easy execution and quick results, the calorimetric method based on the reduction of 3-(4,5-dimethylthiazol-2-yl)-2,5-diphenyl-tetrazolium bromide salt (MTT method) was used for the screening activity. Briefly, 50 µL of culture medium supplemented by 10% FCS and containing $1\times10^4$ MT-4 cells was added to each well of flat bottomed microtitre trays containing 50 µL of medium with or without serial concentrations of the test compounds. 20 µL of a viral suspension was then added to give 100 $CCID_{50}$/well. After 4 days incubation at 37° C., the number of viable MT-4 cells was determined by the MTT method.
Evaluation of Long-Term Anti-HIV-1 Activity.

To evaluate the ability of compounds to extinguish the infection, the following experimental conditions were followed. $10^6$ MT-4 cells were infected at 20° C. for 1 hr with a very high virus load (up to 10 $CCID_{50}$/cell; 1 $CCID_{50}$= 25–250 infectious virions), in the absence or in the presence of test compounds. At the end of infection, the cells were extensively washed and then resuspended in the absence or in the presence of test compounds at a density of $2\times10^5$ cells/mL. 50 µL of the cell suspension, containing $1\times10^4$ MT-4 cells, was added to each well of flat bottomed microtitre trays containing 50 µL of medium with or without serial dilution of the test compounds, alone or in combination. After 1 hour at 37° C. and at intervals during the successive 18 hours, sets of duplicate cultures were resuspended in the absence of the inhibitors and cultivated in drug-free medium thereafter (reverted cultures). After 4 days, surviving cultures were entirely sub-cultivated in fresh medium to bring cells back to initial density ($2\times10^5$ cells/mL) and allow exponential growth. The whole sample (0.1 mL) was resuspended in 0.9 mL of fresh medium containing the given drug concentrations and seeded in 24 multiwell plates. After 4 more days, the whole culture (1.0 mL) was resuspended in 9 mL of fresh medium (containing the given drug concentrations) in a 25-$cm^2$ flask. Starting at day 12, only one-tenth (in 25-$cm^2$ flasks) or one hundredth (in 24 multiwell plates) of each culture was further transplanted. For 4 weeks, at 4 days intervals, the anti-HIV activity of test compounds, alone and in combination, was evaluated by determining the following parameters: p24 levels; virus-induced cytopathogenicity; infectious virus yield; DNA and RNA viral sequences (by PCR).

It is worth noting that the above procedure, while providing conditions suitable for continuous exponential growth of the cultures, allowed all the cells which were originally infected (or the virus produced by them) to survive up to day 12 post infection (p.i.) and beyond.

Results

FIG. 1 is a three dimensional line graph showing the levels of viral p24 in cell culture supernatants treated with the specified concentrations of MC 1220. $10^6$ MT-4 cells were infected with a very high virus in the absence or in the presence of MC 1220. At the end of infection, the cells were extensively washed and then resuspended in the absence or in the presence of test compounds at a density of $2\times10^5$ cells/mL. 50 μL of the cell suspension, containing $1\times10^4$ MT-4 cells, was added to each well of flat bottomed microtitre trays containing 50 μL of medium with or without serial dilution of the MC 1220, alone or in combination. After 1 hour at 37° C. and at intervals during the successive 18 hours, sets of duplicate cultures were resuspended in the absence of the inhibitors and cultivated in drug-free medium thereafter (reverted cultures). After 4 days, surviving cultures were entirely sub-cultivated in fresh medium to bring cells back to initial density ($2\times10^5$ cells/mL) and allow exponential growth. The whole sample (0.1 mL) was resuspended in 0.9 μL of fresh medium containing the given drug concentrations and seeded in 24 multiwell plates. After 4 more days, the whole culture (1.0 mL) was resuspended in 9 mL of fresh medium (containing the given drug concentrations) in a 25-cm$^2$ flask. Starting at day 12, only one-tenth (in 25-cm$^2$ flasks) or one hundredth (in 24 multiwell plates) of each culture was further transplanted. For 4 weeks, at 4 days intervals, the anti-HIV activity of test compounds, alone and in combination, was evaluated by determining p24 levels. The levels of p24 viral protein were determined in the cell-free culture supernatants using the HIV-1 p24 antigen enzyme-linked immunosorbent assay kit (ELISA, Abbott). MC 1220 was able to maintain a sustained reduction of p24 in the culture supernatants at a concentration of 3.5 μM.

FIG. 2 is a three dimensional line graph showing the levels of viral p24 in cell culture supernatants treated with the specified concentrations of Nevirapine. Following the methods of FIG. 1, the levels of p24 viral protein were determined in the cell-free culture supernatants using the HIV-1 p24 antigen enzyme-linked immunosorbent assay kit (ELISA, Abbott). Culture supernatants were harvested at four day intervals, and the amount of p24 present in the supernatant was quantified. Nevirapine was able to maintain a sustained reduction of p24 in the culture supernatants at a concentration of 300 μM, approximately 86 fold higher than MC 1220.

FIG. 3 is a three dimensional line graph showing the levels of viral p24 in cell culture supernatants treated with the specified concentrations of MC-1047. Following the methods of FIG. 1, the levels of p24 viral protein were determined in the cell-free culture supernatants using the HIV-1 p24 antigen enzyme-linked immunosorbent assay kit (ELISA, Abbott). Culture supernatants were harvested at four day intervals, and the amount of p24 present in the supernatant was quantified. MC-1047 was able to maintain a sustained reduction of p24 in the culture supernatants at a concentration of 10 μM.

Example 17

Evaluation of Reverse Transcriptase Activity

Activity against RT can be evaluated in assays with enzymes obtained from partially purified high titer virus stocks prepared in MT-4 cells. Alternatively, recombinant RT (rRT) can be used. Assays with virion purified RT are performed at 37° for 30 min. in a 50 μL reaction mixture containing 50 mM Tris-HCl (pH 8.4), 1 mM dithiothreitol, 80 mM KCl, 6 mM MgCl$_2$, 0.5 mCi [$^3$H]-dTTP (400 Ci/mmol), 0.05 OD$_{260}$ units/mL of Poly(rA)-oligo(dT)$_{10}$, 0.1% Triton x-100, test compounds and 0.006 units of enzyme. 40 μL aliquots are spotted on glass fiber filters (Whatman GF/A) and processed for determination of trichloroacetic acid-insoluble radioactivity. Assays with rRT, in the same reaction mixture contain [methyl-$^3$H]-dTTP (46 Ci/mmol, ICN), or [1',2',3'-$^3$H]-dGTP (42 Ci/mmol, ICN), 0.05 OD$_{260}$ units/mL of Poly(rA)-oligo(dT)$_{10}$ or Poly(rC)-oligo(dG)$_{12-18}$ (Pharmacia).

Formulations

The amount of DABO incorporated into the compositions of the present invention will depend upon the mode of administration, and the desired rate of release of the DABO. Because the composition acts topically, its final concentration will depend on the availability of the compound to bind HIV, in the particular composition employed. Generally speaking, a preferred dose of the composition will be in the range which delivers from about 50 to about 2500 mg, preferably from about 50 to about 1000 mg, and more generally from about 5 to about 5000 mg. The effective dosage range of the pharmaceutically acceptable salts and prodrugs can be calculated based on the weight of the parent drug to be delivered. If the salt or prodrug exhibits activity in itself, the effective dosage can be estimated as above using the weight of the salt or prodrug, or by other means known to those skilled in the art.

It is preferable to administer the active ingredient in conjunction with a pharmaceutically acceptable diluent or carrier, as a pharmaceutical formulation. The present invention thus also involves the use of a pharmaceutical formulation or composition comprising the active ingredient together with one or more pharmaceutically acceptable carriers or diluents and, optionally, other prophylactic ingredients. The carrier(s) or diluent(s) should be "acceptable" in the sense of being compatible with the other ingredients of the formulation and not deleterious to the recipient.

Pharmaceutical formulations include those suitable for vaginal, rectal or topical administration. The formulations may, where appropriate, be conveniently presented in discrete dosage units and may be prepared by any of the methods well known in the art of pharmacy. All such methods include the step of bringing into association the active ingredient with liquid carriers, gels or finely divided solid carriers or both and then, if necessary, shaping the product into the desired formulation.

Pharmaceutical formulations and preparations suitable for administration may conveniently be presented as a solution, an aqueous or oily suspension, or an emulsion. The active ingredient may also be presented as a bolus, electuary or paste. Liquid preparations for vaginal or rectal administration may contain conventional additives such as suspending agents, emulsifying agents, non-aqueous vehicles (which may include edible oils) or preservatives.

Pharmaceutical formulations suitable for rectal or vaginal administration, wherein the carrier is a solid, are most preferably represented as unit dose suppositories. Suitable carriers include cocoa butter and other materials commonly used in the art, and the suppositories may be conveniently formed by admixture of the active compound with the softened or melted carrier(s) followed by chilling and shaping in molds.

Although aqueous gel formulations (described in more detail below) are preferred for "stand-alone" compositions that are not packaged with condoms, anti-viral compositions that are packaged with condoms do not require gels. A lubricant composition packaged with a condom requires only a water-soluble lubricating agent, such as glycerin or propylene glycol. Other components, such as water and a thickening agent, may be added to a condom lubricant if desired.

For "stand-alone" lubricants (i.e., lubricants that are not pre-packaged with condoms), gels and similar aqueous formulations are generally preferred, for various reasons (both scientific and economic) known to those skilled in the art. While the carrier substance used in a particular lubricant is not critical to this invention, in a preferred embodiment the carrier fluid of a lubricant gel as disclosed herein comprises (a) water, (b) a thickening agent, and (c) a lubricating agent.

Preferred thickening agents include cellulose or a chemically treated derivative of cellulose. Derivatives of cellulose which have been chemically treated to make them more hydrophilic (such as hydroxyethyl and hydroxymethyl derivatives, which have numerous additional hydroxy groups bonded to the starting cellulose molecules) have been widely used as thickening agents in gels that are applied to the skin. Other suitable thickening agents include acacia, agar, alginate, carrageenan, gum tragacanth, xanthan gum, collagen, carboxypolymethylene, glyceryl monostearate, polyvinylpyrrolidone, and polyacrylamide. The thickening agents listed above are relatively inactive biologically, and basically serve as carrier substances.

As used herein, "lubricating agent" refers to a component which is incorporated into a genital lubricant for the purpose of reducing friction during intercourse. Although any liquid (including water) sometimes functions as a "lubricant" in the broadest sense of the word, four characteristics distinguish a preferred lubricating agent, for purposes hereof, from water and other liquids that do not have the characteristics preferred for effective and comfortable lubrication during sexual intercourse. A preferred lubricating agent: (1) is substantially more viscous than water and feels slippery when rubbed between two skin surfaces; (2) has an affinity for human skin, and when applied to skin, it spreads smoothly and evenly across the contacted area; (3) remains in contact with the skin, clinging to it in a more substantial manner than water, which is easily wiped away; and, (4) has a low level of volatility, and does not evaporate quickly or become sticky.

The foregoing characteristics can be easily recognized and understood, on a practical level, by rubbing a conventional lubricating agent (such as glycerin or mineral oil) between the fingers. The nature and the durability of the lubrication, and the differences between such agents and other liquids such as plain water, are readily apparent.

In addition, in order to be physiologically acceptable, preferred lubricating agents are gradually broken down into innocuous substances in the body (in cases in which they are absorbed by tissue to a significant degree through the skin or mucous membranes), or they are of a nature that allows them to be secreted by the vagina and washed cleanly from the skin. In either case, they do not foul or clog the pores in skin or mucous membranes, leave any unacceptable residues, or cause other adverse effects if used repeatedly over a span of months, during numerous acts of intercourse.

Several lubricating agents which are used in commercially available sexual lubricants satisfy these criteria, including glycerin (also called glycerine, glycerol, 1,2,3-propanetriol, and trihydroxypropane) and certain types of polyethylene glycol (PEG), such as PEG 200 or PEG 400 (the numbers indicate different molecular weight averages). Various other polymers (such as polypropylene glycol, polyisobutene, and polyoxyethylene) and certain naturally-occurring compounds (such as behenic acid, derived from various types of seeds and animal fats) and their derivatives (such as behenyl alcohol) are also used as lubricants in cosmetics and other formulations that contact the skin. In addition, some sugar-alcohols such as sorbitol, and some silicon compounds such as polydimethylsiloxane, are also used as skin-contacting lubricating agents.

Other components, including preservatives (such as chlorhexidine gluconate), anti-crystallization agents (such as glucono-delta-lactate), fragrances, coloring agents, alkaline or acidic or buffering agents to maintain the proper pH, and soothing or anti-swelling agents (such as lanolin, aloe vera extract, or hydrocortisone) can be added to the compositions described herein.

Various forms of packaging may be used for the articles of manufacture disclosed herein. By way of illustration, a variety of different packages are used for (i) condoms, which are usually packaged in sealed plastic or foil packages with a single condom in each sealed sterile package; and (ii) "stand-alone" lubricants.

In a preferred embodiment, a "stand-alone" lubricant is packaged, shipped, and handled in a package that renders it convenient and useful as a lubricant during intercourse. Types of packaging that are commonly used for stand-alone gels and similar formulations include:

(1) A watertight tube made of deformable metallic foil or plastic walls. Such tubes usually are sealed at one end by means such as crimping, and have an outlet orifice at an opposed second end, which can be covered and sealed by a removable and/or openable device such as a threaded or flip-top cap.

(2) A small, flat, watertight packet which contains a sufficient quantity of lubricant for a single use during intercourse (such as about 5 to 10 milliliters, or about 1 to 2 teaspoons). Such packets can be made of plastic, metallized foil, or other suitable material.

(3) A small single-dose container made of a breakable plastic or other material, which can be opened by breaking off a component that protrudes outwardly from the container, thereby unsealing an outlet orifice.

(4) A stiff-walled bottle, normally but not necessarily in an upright configuration, with a wall (typically cylindrical or with an elliptical or similar cross-sectional shape) made of plastic, glass, or other suitable material.

Another preferred embodiment of genital lubricants that contain an anti-viral composition involves condom lubricants. As used herein, "condom lubricant" refers to a fluidized substance that is spread across one or more surfaces of a condom, and which is contained within a sealed watertight package that contains a condom. In other words, "condom lubricant" refers to lubricants that are pre-packaged with condoms, and does not include "stand-alone" lubricants packaged without condoms, as described above.

This invention has been described with reference to its preferred embodiments. Variations and modifications of the invention will be obvious to those skilled in the art from the foregoing detailed description of the invention.

What is claimed is:

1. A method for inhibiting sexual transmission of HIV comprising topically applying to the skin or epithelial tissue of a human an effective amount of a dihydro-alkyloxy-benzyl-oxopyrimidine of formula (A):

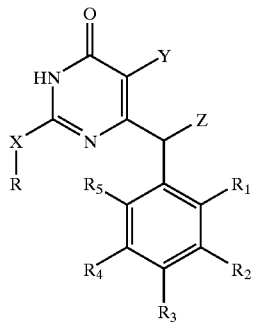

(A)

wherein:
a) X is —NK²;
b) K² is —H, —C₁₋₄alkyl, —C₃₋₆cycloalkyl, or a bond when X—R is N↑O;
c) R is —H, —C₁₋₄alkyl (optionally containing one or more of heteroatoms selected from O, S, and N), —C₃₋₆cycloalkyl (optionally containing one or more of heteroatoms selected from O, S, and N), -aryl, -arylalkyl, heterocycle, or oxo;
d) Y is —H, —C₁₋₄alkyl, or —C₃₋₆cycloalkyl;
e) Z is —H, —C₁₋₄alkyl, or —C₃₋₆cycloalkyl;
f) R₁, R₂, R₃, R₄, and R₅, are independently selected from —H, —C₁₋₄alkyl, -halogen, —NO₂, —OW, or —SW; and
g) W is —H, —CH₃, or -aryl.

2. The method of claim 1 wherein the composition is applied to the vaginal endothelium, the rectal endothelium, or the male genitalia.

3. The method of claim 1 wherein the composition is in the form of a cream, lotion, gel, or foam.

4. The method of claim 1 wherein the composition is in the form of an intra-vaginal pill, an intra-rectal pill, or a suppository.

5. The method of claim 1 wherein the composition is topically applied by release from an intravaginal device selected from a vaginal ring, a vaginal sponge, a diaphram, or a cervical cap.

6. The method of claim 1 wherein the composition is topically applied from the exterior surface of a condom or vaginal applicator.

7. The method of claim 1 wherein the composition further comprises a second anti-HIV agent, a viruside effective against viral infections other than HIV, andlor a spermicide.

8. The method of claim 1 wherein the composition further comprises a lubricant.

9. The method of claim 1 wherein, in formula (A), Y is —C₁₋₄alkyl, and Z is —C₁₋₄alkyl.

10. The method of claim 1 wherein, in formula (A), R₁ and R₅ are halogen.

11. The method of claim 1 wherein, in formula (A), Y is methyl, Z is methyl, R₁ and R₅ are fluorine, and R₂, R₃, and R₄ are hydrogen.

12. The method of claim 1 wherein, in formula (A), —X—R is —N-Me₂ Y is methyl, Z is methyl, R₁ and R₅ are fluorine, and R₂, R₃, and R₄ are hydrogen.

13. The method of claim 1 wherein, in formula (A), —X—R is —NH-cPe, Y is methyl, Z is methyl, R₁ and R₂ are fluorine, and R₂, R₃, and R₄ are hydrogen.

14. The method of claim 1 wherein, in formula (A), —X—R is —N=O, Y is methyl, Z is methyl, R₁ and R₅ are fluorine, and R₂, R₃, and R₄ are hydrogen.

15. A topical composition in the form of a cream, lotion, gel, or foam, comprising a dihydro-alkyloxy-benzyl-OXOPYrlmidine of formula (A):

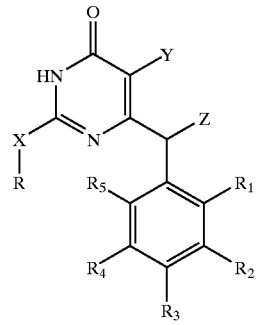

(A)

wherein:
a) X is —NK²;
b) K² is —H, —C₁₋₄alkyl, —C₃₋₆cycloalkyl, or a bond when X—R is N↑O;
c) R is —H, —C₁₋₄alkyl (optionally containing one or more of heteroatoms selected from O, S, and N), —C₃₋₆cycloalkyl (optionally containing one or more of heteroatoms selected from O, S, and N), -aryl, -arylalkyl, heterocycle, or oxo;
d) Y is —H, —C₁₋₄alkyl, or —C₃₋₆cycloalkyl;
e) Z is —H, —C₁₋₄alkyl, or —C₃₋₆cycloalkyl;
f) R₁, R₂, R₃, R₄, and R₅, are in dependently selected from —H, —C₁₋₄alkyl, -halogen, —NO₂, —OW, or —SW; and
g) W is —H, —CH₃, or -aryl.

16. The composition of claim 15 further comprising a second anti-HIV agent.

17. The composition of claim 15 further comprising a viruside effective against viral infections other than HIV.

18. The composition of claim 15 further comprising a spermicide.

19. The composition of claim 15 further comprising a lubricant.

20. A composition in the form of an intra-vaginal or intra-rectal pill or suppository comprising a dihydro-alkyloxy-benzyl-oxopyrimidine of formula (A):

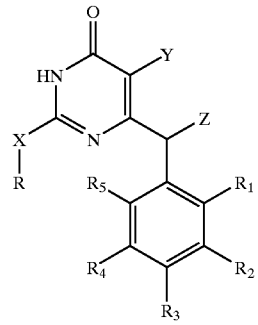

(A)

wherein:
X is —O, —CH₂, —CHK¹ (wherein K¹ is —H, —C₁₋₄alkyl, —C₃₋₆Cycloalkyl), —S, —NK² (wherein K² is —H, —C₁₋₄alkyl, —C₃₋₆cycloalkyl, or a bond when X—R is nitro), -aryl, or -arylalkyl;
R is —H, —C₁₋₄alkyl (optionally containing one or more of heteroatoms selected from O, S, and N), —C₃₋₆cycloalkyl (optionally containing one or more of heteroatoms selected from O, S, N), -aryl, -arylakl, heterocycle, oxo, thio, or a primary amine;

39

Y is —H, —C$_{1-4}$alkyl, or —C$_{3-6}$cycloalkyl;
Z is —H, —C$_{1-4}$alkyl, or —C$_{3-6}$cycloalkyl;
R$_1$ is —H, —C$_{1-4}$alkyl, -halogen, —NO$_2$, —OW (wherein W is —H, —CH$_3$, aryl), or —SW (wherein W is —H, —CH$_3$, -aryl);
R$_2$ is —H, —C$_{1-4}$alkyl, -halogen, —NO$_2$, —OW (wherein W is —H, —CH$_3$, -aryl); or —SW (wherein W is —H, —CH$_3$, -aryl);
R$_3$ is —H, —C$_{1-4}$alkyl, -halogen, —NO$_2$, —OW (wherein W is —H, —CH$_3$, -aryl); or —SW (wherein W is —H, —CH$_3$, -aryl);
R$_4$ is —H, —C$_{1-4}$alkyl, -halogen, —NO$_2$, —OW (wherein W is —H, —CH$_3$, -aryl); or —SW (wherein W is —H, —CH$_3$,-aryl); and
R$_5$ is —H, —C$_{1-4}$alkyl, -halogen, —NO$_2$, —OW (wherein W is —H, —CH$_3$, -aryl), or —SW (wherein W is —H, —CH$_3$, -aryl).

21. The composition of claim 20 further comprising a second anti-HIV agent.

22. The composition of claim 20 further comprising a viruside effective against viral infections other than HIV.

23. The composition of claim 20 further comprising a spermicide.

24. A device for inhibiting the sexual transmission of HIV comprising:
a) a barrier structure for insertion into the vaginal cavity, and
b) a composition comprising a dihydro-alkyloxy-benzyl-oxopyrimidine of formula (A):

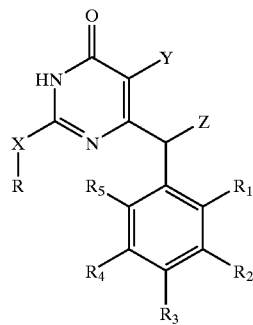

(A)

wherein:
a) X is —NK$^2$;
b) K$^2$ is —H, —C$_{1-4}$alkyl, —C$_{3-6}$cycloalkyl, or a bond when X—R is N↑O;
c) R is —H, —C$_{1-4}$alkyl (optionally containing one or more of heteroatoms selected from O, S, and N), —C$_{3-6}$cycloalkyl (optionally containing one or more of heteroatoms selected from O, S, and N), -aryl, -arylalkyl, heterocycle, or oxo;
d) Y is —H, —C$_{1-4}$alkyl, or —C$_{3-6}$cycloalkyl;
e) Z is —H, —C$_{1-4}$alkyl, or —C$_{3-6}$cycloalkyl;
f) R$_1$, R$_2$, R$_3$, R$_4$, and R$_5$, are in dependently selected from —H, —C$_{1-4}$alkyl, -halogen, —NO$_2$, —OW, or —SW; and
g) W is —H, —CH$_3$, or -aryl.

25. The device of claim 24 wherein the barrier structure is a vaginal sponge, diaphram, cervical cap, or condom.

26. The device of claim 24 wherein the composition further comprises a second anti-HIV agent, a viruside effective against viral infections other than HIV, and/or a spermicide.

40

27. A compound of formula (A):

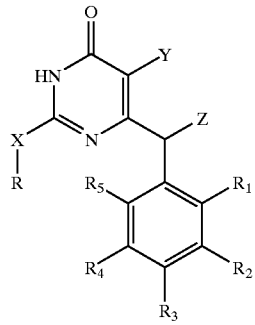

(A)

wherein:
a) —X—R is —N-Me$_2$, Y is methyl, Z is methyl, R$_1$ and R$_5$ are fluorine, and R$_2$, R$_3$, and R$_4$ are hydrogen;
b) —X—R is —N═O, Y is methyl, Z is methyl, R$_1$ and R$_5$ are fluorine, and R$_2$, R$_3$, and R$_4$ are hydrogen; or
c) —X—R is —S-MeSMe, Y is methyl, Z is methyl, R$_1$ and R$_5$ are fluorine, and R$_2$, R$_3$, and R$_4$ are hydrogen.

28. The compound of claim 27 wherein, in formula (A), —X—R is —N-Me$_2$, Y is methyl, Z is methyl, R$_1$ and R$_5$ fluorine, and R$_2$, R$_3$, and R$_4$ are hydrogen.

29. The compound of claim 27 wherein, in formula (A), —X—R is —N↑O, Y is methyl, Z is methyl, R$_1$ and R$_5$ are fluorine, and R$_2$, R$_3$, and R$_4$ are hydrogen.

30. The compound of claim 27 wherein, in formula (A), —X—R is —S-MeSMe, Y is methyl, Z is methyl, R$_1$ and R$_5$ are fluorine, and R$_2$, R$_3$, and R$_4$ are hydrogen.

31. The method of claim 1 wherein the composition is applied prior to sexual intercourse.

32. The composition of claim 15 wherein, in formula (A), Y is —C$_{1-4}$alkyl, and Z is —C$_{1-4}$alkyl.

33. The composition of claim 15 wherein, in formula (A), R$_1$ and R$_5$ are halogen.

34. The composition of claim 15 wherein, in formula (A), Y is methyl, Z is methyl, R$_1$ and R$_5$ are fluorine, and R$_2$, R$_3$, and R$_4$ are hydrogen.

35. The composition of claim 15 wherein, in formula (A), —X—R is —N-Me$_2$ Y is methyl, Z is methyl, R$_1$ and R$_5$ are fluorine, and R$_2$, R$_3$, and R$_4$ are hydrogen.

36. The composition of claim 15 wherein, in formula (A), —X—R is —NH-cPe, Y is methyl, Z is methyl, R$_1$ and R$_5$ are fluorine, an R$_2$, R$_3$, and R$_4$ are hydrogen, and cPe is cyclic pentane.

37. The composition of claim 15 wherein, in formula (A), —X—R is —N↑O, Y is methyl, Z is methyl, R$_1$ and R$_5$ are fluorine, and R$_2$, R$_3$, and R$_4$ are hydrogen.

38. The composition of claim 20 wherein, in formula (A), —X—R is —N-Me$_2$ Y is methyl, Z is methyl, R$_1$ and R$_5$ fluorine, and R$_2$, R$_3$, an R$_4$ are hydrogen.

39. The composition of claim 20 wherein formula (A), —X—R is —NH-cPe, Y is methyl, Z is methyl, R$_1$ and R$_5$ are fluorine, and R$_2$, R$_3$, and R$_4$ are hydrogen, and cPe is cyclic pentane.

40. The composition of claim 20 wherein, in formula (A), —X—R is —N↑O, Y is methyl, Z is methyl R$_1$ and R$_5$ fluorine, and R$_2$, R$_3$ and R$_4$ are hydrogen.

41. The device of claim 24 wherein, in formula (A), —X—R is —N-Me$_2$ Y is methyl, Z is methyl, R$_1$ and R$_5$ are fluorine and R$_2$, R$_3$, and R$_4$ are hydrogen.

42. The device of claim 24 wherein, in formula (A), —X—R is —NH-cPe, Y is methyl, Z is methyl, R$_1$ and R$_5$ fluorine and R$_2$, R$_3$ and R$_4$ hydrogen, and cPe is cyclic pentane.

43. The device of claim 24 wherein, in formula (A), —X—R is —N═O, Y is methyl, Z is methyl, R$_1$ and R$_5$ are fluorine, and R$_2$, R$_3$, and R$_4$ are hydrogen.

* * * * *